United States Patent [19]

Weber et al.

[11] 3,984,399
[45] Oct. 5, 1976

[54] BIS-STILBENE COMPOUNDS

[75] Inventors: Kurt Weber, Basel; Peter Liechti, Arisdorf; Hans Rudolf Meyer, Binningen; Adolf Emil Siegrist, Basel, all of Switzerland

[73] Assignee: Ciba-Geigy AG, Basel, Switzerland

[22] Filed: Sept. 27, 1974

[21] Appl. No.: 509,768

Related U.S. Application Data

[63] Continuation of Ser. No. 347,950, April 4, 1973, abandoned, which is a continuation of Ser. No. 23,056, March 26, 1970, abandoned, which is a continuation-in-part of Ser. No. 763,402, Sept. 27, 1968, abandoned.

[30] Foreign Application Priority Data

Oct. 3, 1967 Switzerland.................. 13806/67
Mar. 27, 1969 Switzerland.................. 4791/69

[52] U.S. Cl.............................. 260/240 CA; 8/1 W; 26/1; 252/108; 260/240 D; 260/456 R; 260/457; 260/465 H; 260/505 R; 260/505 C
[51] Int. Cl.² ........................................ C07D 23/00
[58] Field of Search ...... 260/505 R, 240 CA, 240 D

[56] References Cited

UNITED STATES PATENTS 3,177,208 4/1965 Stilz ..................................... 260/505
3,843,718 10/1974 Luethi ............................ 260/512 C

*Primary Examiner*—James O. Thomas, Jr.
*Assistant Examiner*—A. Siegel
*Attorney, Agent, or Firm*—Joseph G. Kolodny; Edward McC. Roberts; Prabodh I. Almaula

[57] ABSTRACT

The present invention provides the new bis-stilbene compounds, which are useful as optical brighteners and correspond to the formula

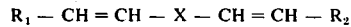

$R_1 - CH = CH - X - CH = CH - R_2$ in which X represents a diphenyl residue bound in positions 4 and 4' to the =CH— groups; $R_1$ and $R_2$ independently of each other, each represents a monocyclic benzene residue, a diphenyl, naphthyl or pyridyl residue, and in which at least one of the cyclic systems $R_1$, $R_2$, X contains a possibly functionally modified sulphonic acid group, a sulphone group, a possibly functionally modified carboxylic acid group, a nitrile, hydroxyl, mercapto or methyl group.

23 Claims, No Drawings

NEW BIS-STILBENE COMPOUNDS

CROSS-REFERENCES TO RELATED APPLICATIONS

This is a continuation of our application Ser. No. 347,950, now abandoned, filed Apr. 4, 1973 which in turn is a continuation of our application Ser. No. 23,056 filed Mar. 26, 1970, now abandoned which in turn is a continuation-in-part of our application Ser. No. 763,402 filed Sept. 27, 1968, now abandoned.

The present invention provides new fluorescent bis-stilbene compounds, which correspond to the formula $$R_1 - CH = CH - X - CH = CH - R_2 \qquad (1)$$

in which X represents a diphenyl residue bound in positions 4 and 4 ' to the =CH— groups; $R_1$ and $R_2$, independently of each other, each represents a monocyclic benzene residue, a diphenyl or naphthalene residue, and in which at least one of the cyclic systems $R_1$, $R_2$, X contains a possibly functionally modified sulphonic acid group, a sulphone group, a possibly functionally modified carboxylic acid group, a nitrile, hydroxyl, mercapto or methyl group.

The compounds of the formula (1) are colorless or may at most be only faintly coloured and must therefore not contain chromophoric groups such as nitro or azo groups or anthraquinone residues. The two residues $R_1$ and $R^2$ may be different from each other, but they are preferably identical. Otherwise, these compounds contain in any desired position at least one and for instance up to four, preferably two of the said substitutents. When they contain four such substitutents, they form advantageously identical pairs and are arranged symmetrically. Thus, for example, the molecule of the bis-stilbene compound may contain in addition to two carboxylic acid groups or preferably two sulphonic acid groups two nitrile groups or two to six methyl groups. Suitable sulphonic acid groups and carboxylic acid groups are the free acid groups of the formula —SO₃—cation and —COO—cation respectively [in which the cation is advantageously hydrogen, alkali metal or ammonia] and the corresponding functionally modified groups such as sulphonic acid and carboxylic acid ester groups especially alkyl ester groups containing 1 to 18 carbon atoms in the alkyl residue, and sulphonic acid amide and carboxylic acid amide groups, and the latter may contain an H₂N or, for example, a mono- or dialkylamide group with 1 to 4 carbon atoms in each alkyl residue. The sulphone groups are in the first place the alkylsulphone groups such as methyl-, ethyl- or phenyl-sulphone.

More specifically, the present invention provides new fluorescent compounds of formula (1) in which X represents a 4,4'-diphenyl residue, $R_1$ and $R_2$, independently of each other, each represents a benzene residue, a diphenyl-4-residue, a naphthyl or a pyridyl residue, at least one of the cyclic systems $R_1$, $R_2$ and X containing a sulphonic acid group, a sulphonic acid amide group, a sulphonic acid ether group, an alkyl sulphone group, the phenyl sulphone group, a carboxylic acid group, a carboxylic acid ester group, a carboxylic acid amide group, a nitrile, hydroxyl, mercapto or methyl group.

Apart from the substituents indicated above the bis-stilbene compounds may contain further substituents, for example halogen atoms such as bromine or especially chlorine atoms; alkoxy groups, especially those containing 1 to 4 carbon atoms such as methoxy, ethoxy; alkyl groups with at least 2 and at most 18 carbon atoms, preferably with 4 carbon atoms, such as ethyl, propyl, isopropyl, n-butyl, tertiary butyl, or trifluoromethyl groups.

The practically important compounds of the formula (1) may be defined by the formula

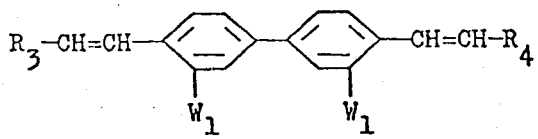

in which $R_3$ represents diphenyl or a residue

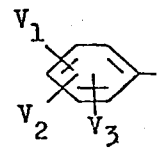

$R_4$ stands for phenyl, diphenylyl, α- or β-naphthyl or for a residue

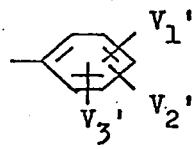

in which $V_1$ and $V_1'$ may be identical or different and each represents hydrogen or an obligatory substitutent Q representing a member selected from the group consisting of a sulphonic acid group, a salt, ester, amide, and a halide thereof, a carboxylic acid group, a salt, ester and an amide thereof; the nitrile group, a sulphone group and a methyl group; $V_2$ and $V_2'$ may be identical or different and each represents hydrogen, an alkyl group with 1 to 18 carbon atoms; an alkoxy group with 1 to 12 carbon atoms, halogen or a sulphonic acid group or its salts, esters or amides; $V_3$ and $V_3'$ may be identical or different and each represents hydrogen or an alkyl group with 1 to 4 carbon atoms; $W_1$ represents hydrogen, an alkyl group containing 2 to 4 carbon atoms; an alkoxy group with 1 to 4 carbon atoms; halogen, or an obligatory substitutent Q representing a member selected from the group consisting of a sulphonic acid group, a salt, an ester, an amide and a halide thereof, a carboxylic acid, a salt, an ester and an amide thereof, the nitrile group, a sulphone group and the methyl group; on condition that at least one of the symbols $V_1$, $V_1'$ or $W_1$ has the significance of an obligatory substitutent Q.

Functionally modified sulphonic acid groups and carboxylic acid groups respectively, as defined herein, are mainly their esters, amides and halides. While in the case of esters of an aromatic or araliphatic nature the phenyl esters (which may be substituted) and benzyl esters are of practical value, the aliphatic esters concerned are in the first place alkyl esters with 1 to 18 carbon atoms.

The amides of the said acids include not only the unsubstituted but also the mono- and disubstituted representatives, and the substituting component may be of an aromatic nature (anilide), an araliphatic and especially also of an aliphatic or cycloaliphatic nature. In this case, too, the aliphatic representatives contain in general no more than 18 carbon atoms and may be substituted by hydroxyl groups, halogen atoms, alkoxy, nitrile, carboxyl, carbalkoxy, sulpho, amino or alkylamino groups.

Among the acid halides the chlorides and bromides are especially noteworthy.

Although among the salts the water-soluble types (alkali metal ammonium or amine salts) are of preeminent importance, other salts may certainly be valuable in certain cases, for example the barium and calcium salts.

From among the sulphones the arylsulphones and aralkylsulphones, such as phenylsulphone and benzylsulphone, as well as alkylsulphones with lower alkyl groups (containing 1 to 4 carbon atoms) may be mentioned.

A halogen substitutent is in the first place a fluorine or chlorine atom.

Particularly valuable compounds of the formula (1) or (2) are those bis-stilbene compounds which are listed under A. and B. respectively:

A. Compounds of the formula (3) 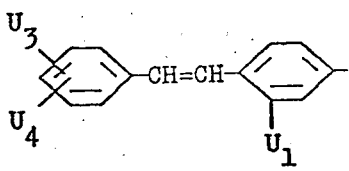

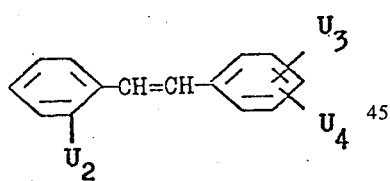

in which at least one and at most two of the symbols $U_1 - U_4$ represent a possibly functionally modified sulphonic acid group, a benzene residue further substituted by a sulphonic acid group, a sulphone group, a possibly functionally modified carboxylic acid group, a nitrile or methyl group and the other symbols $U_{1-4}$, independently of each other, stand for a hydrogen atom, an alkyl group with 1 to 18 carbon atoms, an alkoxy group with 1 to 12 carbon atoms, a chlorine atom, a benzene residue, or two vicinal substituents $U_3 + U_4$ stand for a methylenedioxy group.

B. Compounds of the formula (4) 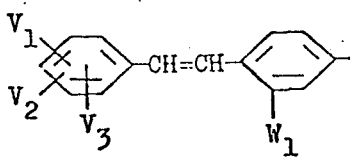

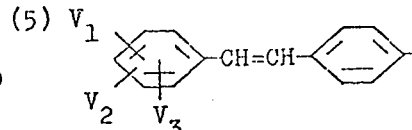

in which $V_1$ represents hydrogen or an obligatory substituent Q representing a member selected from the group consisting of a sulphonic acid group, a salt, ester, amide, and a halide thereof, a carboxylic acid group, a salt, ester and an amide thereof; the nitrile group, a sulphone group and a methyl group; $V_2$ represents hydrogen; an alkyl group with 1 to 18 carbon atoms; an alkoxy group with 1 to 12 carbon atoms, halogen or a sulphonic acid group or its salts, esters or amides; $V_3$ represents hydrogen or an alkyl group with 1 to 4 carbon atoms, $W_1$ represents hydrogen, an alkyl group containing 2 to 4 carbon atoms; an alkoxy group with 1 to 4 carbon atoms; halogen, for an obligatory substituent Q representing a member selected from the group consisting of a sulphonic acid group, a salt, an ester, an amide and a halide thereof, a carboxylic acid, a salt, an ester and an amide thereof, the nitrile group, a sulphone group and the methyl group; on condition that at least one of the symbols $V_1$ or $W_1$ has the significance of an obligatory substituent Q.

Within the above formulae two important subgroups should be mentioned especially, in one of which the central diphenylene member is unsubstituted (Types C to H), while the other group contains the obligatory substituents according to formula (1) in the central diphenylene member (Types J to N). These two groups comprise the following compounds:

C. Compounds of the formula (5) 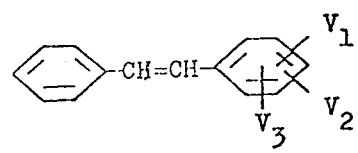

in which $V_1$ represents a sulphonic acid group or its salts, esters, amides or halides, a carboxylic acid group or its salts, esters or amides, the nitrile group, a sulphone or methyl group; $V_2$ represents hydrogen, an alkyl group with 1 to 18 carbon atoms, an alkoxy group with 1 to 12 carbon atoms, halogen or a sulphonic acid group or its salts, esters or amides, and $V_3$ represents hydrogen or an alkyl group with 1 to 4 carbon atoms.

D. Compounds of the formula (6)

in which $U_3$ represents a possibly functionally modified subphonic acid group, a benzene residue substituted by a sulphonic acid group; a sulphone group, a possibly functionally modified carboxyl acid group, a nitrile or methyl group, and $U_4$ represents one of the substituents just indicated for $U_3$ or a hydrogen atom, an alkyl group with 2 to 8 carbon atoms, an alkoxy group with 1 to 12 carbon atoms, a chlorine atom or a benzene residue.

E. Compounds of the formula (7) 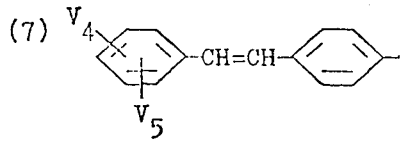

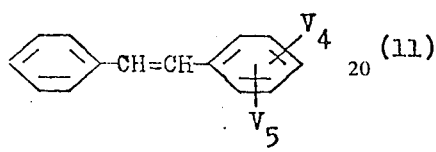

in which $V_4$ represents a sulphonic acid group or its salts, esters or amides, a carboxylic acid group or its salts, esters or amides or the nitrile group; $V_5$ represents hydrogen or a sulphonic acid group or its salts, esters or amides, an alkyl group with 1 to 4 carbon atoms or an alkoxy group with 1 to 4 carbon atoms.

F. Compounds of the formula (8) 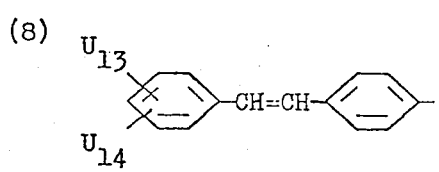

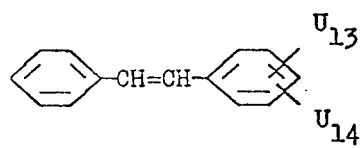

in which $U_{13}$ represents a sulphonic acid group and $U_{14}$ a hydrogen or chlorine atom or an alkyl group with 1 to 4 carbon atoms.

G. Compounds of the formula (9) 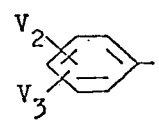

in which Y is a cation and the $YO_3S—$ groups are preferably in ortho-position to the $—CH=$ groups.

H. Compounds of the formula

(10) 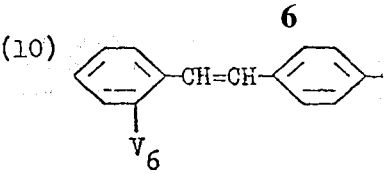

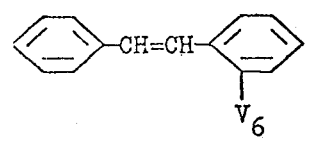

in which $V_6$ represents a sulphonic acid group or a salt or amide thereof.

J. Compounds of the formula

(11) 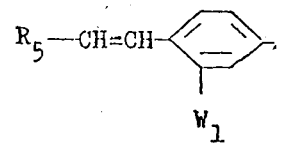

in which $R_5$ represents either a naphthyl residue or the residue and in which $V_2$ represents hydrogen, an alkyl group with 1 to 12 carbon atoms, halogen or sulphonic acid group or a salt, ester or amide thereof; $V_3$ represents hydrogen or an alkyl group containing 1 to 4 carbon atoms, and $W_1$ represents a sulphonic acid group or a salt, ester or amide thereof, the methyl group, a carboxyl group or a salt, ester or amide therof or the nitrile group, wherein furthermore $W_1$ may represent an alkyl group with 2 to 4 carbon atoms, an alkoxy group with 1 to 4 carbon atoms or halogen, provided that $V_2$ stands for a sulfonic acid group or its salts, esters or amides or for the methyl group.

K. Compounds of the formula (12)

in which one of the symbols $U_5$, $U_6$ and $U_7$ represents a possibly functionally modified sulphonic or carboxylic acid group or a nitrile group and the two others represent hydrogen atoms.

L. Compounds of the formula (13)

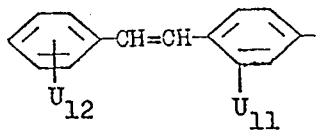

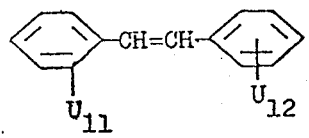

in which one of the symbols $U_{11}$ or $U_{12}$ represents a sulphonic acid group and the other a hydrogen or chlorine atoms, an alkyl group containing 1 to 4 carbon atoms or a nitrile group.

M. Compounds of the formula (14)

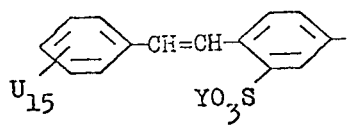

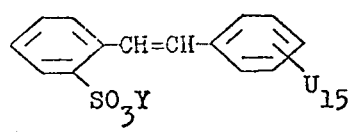

in which $U_{15}$ represents a hydrogen or chlorine atom, a nitrile group, an alkyl or alkoxy group with 1 to 4 carbon atoms, a phenyl group which may contain sulphonic acid groups, a phenoxy group, a benzene residue or a possibly functionally modified carboxylic acid group and Y represents a cation.

N. Compounds of the formula (15)

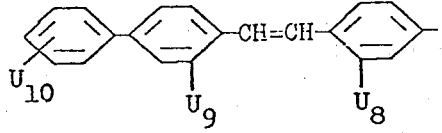

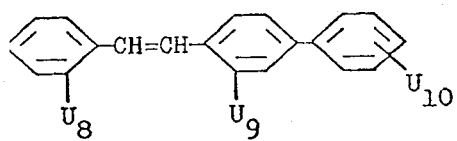

in which one or two of the symbols $U_{8-10}$ represent a sulphonic acid group and the other two symbols represent atoms, or the other symbol stands for a hydrogen atom.

Another aspect of the present invention concerns compounds of the type according to the general formula (1), which are characterised by asymmetric substitution relative to the central grouping

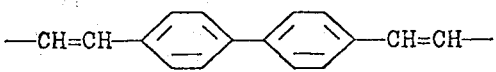

in the formula (1), especially by the presence of only one sulphonic acid group (as a substituent in one phenyl group) in one of the two radicals which are bonded to the said central grouping.

The said compounds of asymmetrical structure correspond to the formula (16)

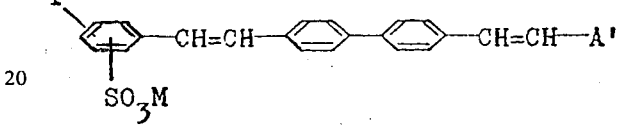

wherein A' represents an α-naphthyl, β-naphthyl, pyridyl or 4-diphenylyl radical or a radical of formula

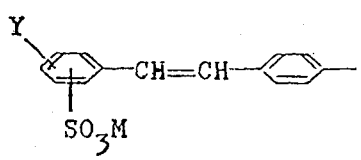

wherein $X_1$ represents hydrogen, an alkyl group containing 1 to 4 carbon atoms with the exception of the p-isopropyl group, halogen, alkoxy with 1 to 4 carbon atoms, sulphonic acid dialkylamide, sulphonic acid alkyl esters, sulphone, a carboxylic acid group as well as its salts, esters or amides, trifluoromethyl or a nitrile group in the m- or o-position, $X_2$ and $X_3$ represent hydrogen, an alkyl group containing 1 to 4 carbon atoms with the exception of the p-isopropyl group, halogen, or alkoxy with 1 to 4 carbon atoms, or $X_2$ together with $X_3$ forms a methylenedioxy group, M represents a salt-forming cation and Y represents a hydrogen atom, halogen, an alkyl group containing 1 to 4 carbon atoms or an alkoxy group containing 1 to 4 carbon atoms.

Within the framework of formula (16), the following sub-groups of compounds are of interest:

a. Compounds of formula (17)

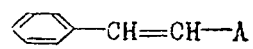

wherein A represents an α-naphthyl, β-naphthyl or 4-diphenylyl radical or a radical of formula

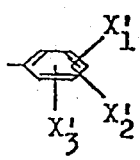

wherein X₁' represents hydrogen, methyl, tert.butyl, halogen, alkoxy with 1 to 4 carbon atoms, sulphonic acid dialkylamide, sulphonic acid alkyl esters, sulphone, or a carboxylic acid group as well as its salts, esters or amides, X₂' represents hydrogen, methyl, tert.butyl halogen or alkoxy with 1 to 4 carbon atoms and X₃' denotes hydrogen, methyl or halogen, M represents a salt-forming cation and Y represents a hydrogen atom, halogen, an alkyl group containing 1 to 4 carbon atoms or an alkoxy group containing 1 to 4 carbon atoms. Amongst the abovementioned functional derivatives of carboxylic acids, that is to say salts, esters and amides, the alkyl esters with 1 to 18 carbon atoms, aralkyl esters with 1 to 4 carbon atoms in the alkyl part (aryl mostly being represented by phenyl) and phenyl esters are of importance, whilst in the case of the amides the unsubstituted amide group —CONH₂ as well as monoalkylamides and dialkylamides (containing 1 to 18 carbon atoms), cycloalkylamides, amides of the morpholide type, phenylalkylamides (with 1 to 4 carbon atoms in the alkyl. part) and anilide types, optionally substituted by hydroxyl groups and nitrile groups, deserve mention. Amongst the sulphones, phenylsulphone and alkylsulphones with 1 to 6 carbon atoms in the alkyl group deserve special mention. Possible salts are especially those of the alkali metals (for example Na or K) and of ammonium, amine salts such as for example salts of the alkylamines or alkanolamines (triethanolamine), and pyridine salts. Alkaline earth metal salts (for example Ca or Ba) can optionally also be used.

b. Compounds which contain the sulphonic acid group in the o-position to the stilbene double bond and which hence correspond to the formula (18)

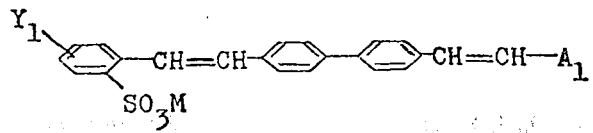

wherein A₁ represents an α-naphthyl, β-naphthyl or 4-diphenylyl radical or a radical of formula

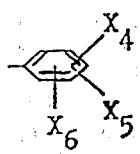

wherein X₄ denotes hydrogen, methyl, tert.butyl, fluorine, chlorine, alkoxy with 1 to 4 carbon atoms, sulphonic acid dialkylamide with 1 to 4 carbon atoms in the alkyl groups, sulphonic acid alkyl esters with 1 to 12 carbon atoms in the alkyl group, sulphone or a carboxylic acid group as well as its salts, esters or amides with up to 12 carbon atoms, X₅ denotes hydrogen, methyl, tert.butyl, fluorine, chlorine or alkoxy with 1 to 4 carbon atoms and X₆ denotes hydrogen, methyl, fluorine or chlorine, M represents a salt-forming cation and Y₁ represents a hydrogen atom, fluorine, chlorine, an alkyl group containing 1 to 4 carbon atoms or an alkoxy group containing 1 to 4 carbon atoms.

c. Compounds which correspond to the formula (19)

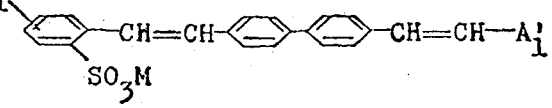

wherein A₁' represents a β-naphthyl, pyridyl, or 4-diphenylyl radical or a radical of formula

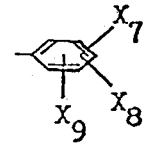

wherein X₇ represents hydrogen, an alkyl group containing 1 to 4 carbon atoms with the exception of the p-isopropyl group, fluorine, chlorine, alkoxy with 1 to 4 carbon atoms, sulphonic acid dialkylamide with 1 to 4 carbon atoms in the alkyl groups, sulphonic acid alkyl esters with 1 to 4 carbon atoms in the alkyl group, sulphone, a carboxylic acid group as well as its salts, esters or amides with up to 12 carbon atoms, or a nitrile group in the m- or o-position, X₈ and X₉ represent hydrogen, an alkyl group containing 1 to 4 carbon atoms with the exception of the p-isopropyl group, fluorine, chlorine or alkoxy with 1 to 4 carbon atoms, M represents a salt-forming cation and Y₁ represents a hydrogen atom, fluorine or chlorine, an alkyl group containing 1 to 4 carbon atoms or an alkoxy group containing 1 to 4 carbon atoms.

Particularly preferred compounds according to formula (16) are those which correspond to the formula (20)

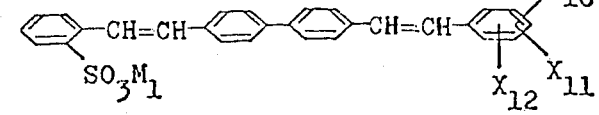

wherein X₁₀ represents hydrogen, methyl, tert.butyl, alkoxy with 1 to 4 carbon atoms, sulphonic acid dialkylamide with alkyl groups containing 1 to 4 carbon atoms, alkylsulphone with 1 to 4 carbon atoms, carboxyl, carbalkoxy with 1 to 4 carbon atoms in the alkyl part, nitrile in the o- or m-position, phenyl, fluorine or chlorine, X₁₁ denotes hydrogen, methyl, alkoxy with 1 to 4 carbon atoms or chlorine, X₁₂ denotes hydrogen or methyl and $M_1$ represents a salt-forming cation from the group of hydrogen ion, alkali metal ion, ammonium ion or amine salt ion, as well as compounds which correspond to the formula (21)

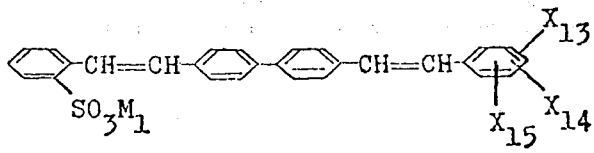

wherein $X_{13}$ denotes hydrogen, methyl, alkoxy with 1 to 4 carbon atoms, sulphonic acid dialkylamide with alkyl groups containing 1 to 4 carbon atoms or chlorine, $X_{14}$ denotes hydrogen, methyl, alkoxy with 1 to 4 carbon atoms or chlorine, $X_{15}$ denotes hydrogen, methyl or alkoxy with 1 to 4 carbon atoms and $M_1$ represents a salt-forming cation from the group of hydrogen ion, alkali metal ion, ammonium ion or amine salt ion. Within the alkoxy groups in the above formulae (20) and (21) methoxy groups, above all in the o- and/or m-position, are of preferred significance.

Compounds for specific purposes are those corresponding to the formula

(22) 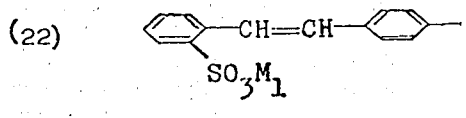

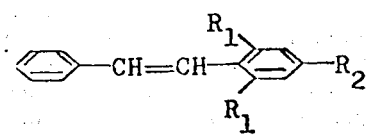

wherein $R_2$ denotes hydrogen, methyl, methoxy, sulphonic acid dialkylamide with alkyl groups containing 1 to 4 carbon atoms or chlorine, $R_1$ denotes hydrogen, methyl, methoxy or chlorine and $M_1$ represents a salt-forming cation from the group of hydrogen ion, alkali metal ion, ammonium ion or amine salt ion, as well as compounds which correspond to the formula

(23) 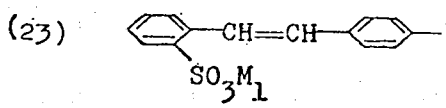

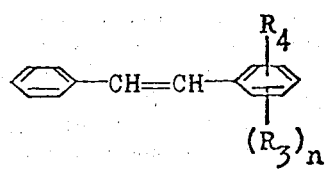

wherein $R^3$ represents hydrogen, methyl, methoxy or chlorine, $n$ denotes the numbers 1 or 2, with $R_3$ preferably being in the o- or m-position, $R_4$ denotes hydrogen, fluorine, phenyl, carboxyl, carboxymethyl, sulphonic acid dimethylamido or a nitrile group located in the o- or m-position, and $M_1$ represents a salt-forming cation from the group of hydrogen ion, alkali metal ion, ammonium ion or amine salt ion.

The bis-stilbene compounds of the formulae (1) to (15) are accessible by known methods. In general, a compound of the formula (24) $Z_1 - X - Z_1$ is reacted at a molecular ratio of 1:2 with a compound of the formula (25) $R_1 - Z_2$ or (26) $Z_2 - R_2$ in which X represents a diphenyl residue bound with $Z_1$ in positions 4 and 4'; $R_1$ and $R_2$ each represents a monocyclic benzene residue, a diphenyl or naphthalene residue, one of the symbols $Z_1$ or $Z_2$ stand for an O=CH— group and the other for a grouping of the formulae

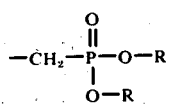 (27)

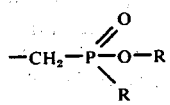 (28)

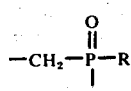 (29)

or

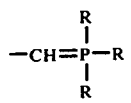 (30)

in which R represents a possibly further substituted alkyl residue, preferably containing 1 to 6 carbon atoms, an aryl residue, preferably a phenyl residue, a cycloalkyl residue, preferably a cyclohexyl residue or an aralkyl residue, preferably a benzyl residue, and where at least one of the cyclic sstems present in the starting materials contains a possibly functionally modified sulphonic acid group, a sulphone group, a possibly functionally modified carboxyl acid group, a nitrile, hydroxyl, mercapto or methyl group (as also defined in the above description of the substances), and, if desired, further reactions are carried out on these substituents.

Thus, for example, a dialdehyde of the formula

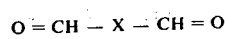 (31)

may be reacted with a monofunctional compound of the formula $$R_1 - V, \quad (32)$$

or a monoaldehyde of the formula $$R_1 - CH = O \quad (33)$$

with a bifunctional compound of the formula $$V - X - V \quad (34)$$

in which formulae X and $R_1$ have the above meanings and V represents a phosphoriferous substituent of the formula (27), (28), (29) or (30).

The relevant starting materials, that is to say the phosphorus compounds of the formula (32) and (34), are obtained when a halomethyl compound, preferably a chloromethyl compound, of the formula $$R_1 - CH_2 - \text{halogen} \quad (35)$$

or $$\text{halogen} - CH_2 - X - CH_2 - \text{halogen} \quad (36)$$

is reacted with a phosphorus compound of the formula

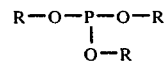   (37)

or

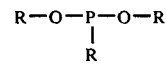   (38)

or

   (39)

in which formulae R has the above meaning, and oxygen-linked residues R are preferably lower alkyls, and residues R linked directly with phosphorus, on the other hand, are preferably aryl residues such as benzene residues.

The reactions required for the manufacture of the starting materials and those for the manufacture of the final products may be carried out in the usual manner.

Thus, there are two main variants available for the manufacture of the compounds of the formula (2) of special practical value; they are characterized in that either a compound of the formula

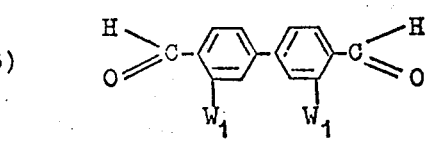   (40)

is reacted at a molecular ratio of 1 : 2 with a compound of the formula $$R_3 - CHO \quad (41)$$

or $$R_4 - CHO \quad (42)$$

or a compound of the formula

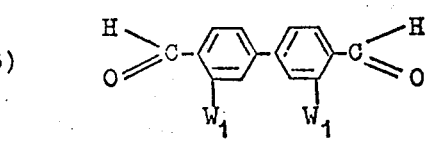   (43)

is reacted at a molecular ratio of 1 : 2 with a compound of the formula $$R_3 - Z_3 \quad (44)$$

or $$Z_3 - R_4 \quad (45)$$

wherein $R_3$, $R_4$ and $W_1$ have the same meanings as defined for the formula (2) and $Z_3$ represents one of the groupings of the formula

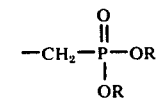   (27)

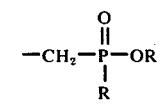   (28)

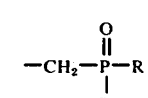   (29)

or

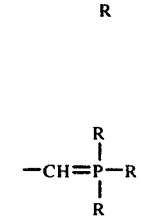   (30)

in which R represents a possibly further substituted alkyl residue, an aryl, cycloalkyl or aralkyl residue.

In either case the reaction is carried out by letting the reactants react together in the presence of a strongly basic alkal metal compound and in the presence of a preferably hydrophilic, strongly polar solvent; when an alkali metal hydroxide is used as the strongly basic alkali metal compound this hydroxide may contain up to 25% of water.

A corresponding process for the manufacture of compounds of the formula (5) is characterized in that the dialdehyde of the formula

(46) 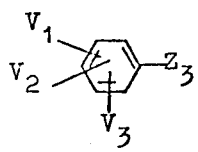

is reacted at a molecular ratio of 1 : 2 with a compound of the formula

(47) 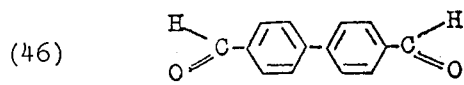

or a compound of the formula

(48) 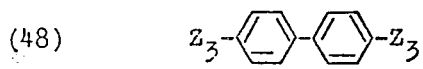

is reacted at a molecular ratio of 1 : 2 with a compound of the formula

(49) 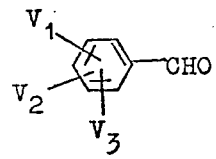

and in either case the reaction is performed as described above.

In a similar manner compounds of the formula (11) are obtained when an aldehyde of the formula

(50) 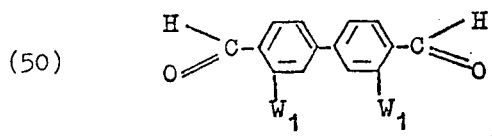

is reacted with a compound of the formula $R_5 - Z_3$ (51)

or a compound of the formula

(52) 

is reacted with an aldehyde of the formula $R_5—CHO$ (53)

and in this case, too, the reaction is performed as described above.

The solvent used in the above-described process for the manufacture of compounds of the formula (1) may be, for example, toluene, xylene, a chlorobenzene, an alcohol such as ethanol, ethyleneglycol monomethyl ether or preferably N-methylpyrrolidone, dimethylformamide, diethylformamide, dimethylacetamide or dimethylsulphoxide.

The temperature at which the reaction is performed may vary within wide limits and depends on ($\alpha$) the stability of the solvent used towards the reactants, especially towards the strongly basic alkali metal compounds, ($\beta$) the reactivity of the condensation partners and ($\gamma$) the efficacy of the combination solvent+base as condensing agent. Advantageously, the reaction temperature is within the range from 30° to 60°C, though in many cases satisfactory results may be obtained even at room temperature (about 20°C) or at a temperature of 100°C or over, and even at the boiling temperature of the solvent, when this is desirable with a view to saving time or when a less active but cheaper condensing agent is to be used. Thus, on principle it is also possible to use a reaction temperature ranging from 10° to 180°C.

Particularly suitable strongly basic alkali metal compounds are the hydroxides, amides and alcoholates (preferably those with primary alcohols containing 1 to 4 carbon atoms); for reasons of economy those of lithium, sodium or potassium will be preferred. In principle it is possible to use successfully in special cases also alkali metal sulphides or carbonates, aryl-alkali metal compounds, for example phenyl-lithium, or strongly basic amides (including ammonium bases, for example trialkyl ammonium hydroxides).

The bis-stilbene compounds according to formula (16) and of the subordinate formula can be manufactured analogously to methods which are in themselves known. In general the procedure followed is that approximately 1 mol equivalent of a compound of formula

(54) 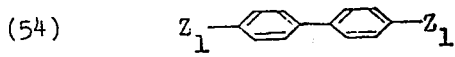

is reacted with approximately 1 mol equivalent of a compound of formula

(55) 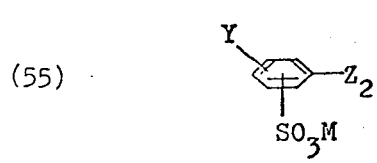

and approximately 1 mol equivalent of a compound of formula $Z_2-A'$ (56)

wherein one of the symbols $Z_1$ and $Z_2$ denote a O=CH— group and the other denotes one of the groupings of formulae

(27) 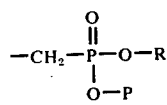

(28) 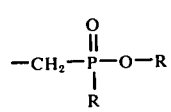

(29) 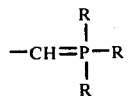

and

(30) —CH=P(R)(R)(R)

wherein R represents an alkyl radical which is optionally substituted further, preferably an alkyl radical with up to 6 carbon atoms, an aryl radical, preferably a phenyl radical, a cycloalkyl radical, preferably a cyclohexyl radical, or an aralkyl radical, preferably a benzyl radical.

The following are obtained in an entirely corresponding manner:

a. Compounds of formula (17) by reaction of 1 mol equivalent of the compound of formula (54) with 1 mol equivalent of the compound according to formula (55) and one mol equivalent of the compound of formula $Z_2-A$ (57)

b. Compounds of formula (18) by reaction of approximately 1 mol equivalent of a compound of formula

(54) 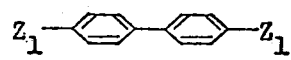

with approximately 1 mol equivalent of a compound of formula

(58) 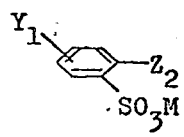

and approximately 1 mol equivalent of a compound of formula $Z_2-A_1$ (59)

c. Compounds of formula (19) by reaction of approximately 1 mol equivalent of a compound of formula

(54) 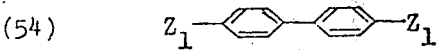

with approximately 1 mol equivalent of a compound of formula

(58) 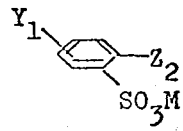

and approximately 1 mol equivalent of a compound of formula

(60)     $Z_2$—$A_1'$ or d. compounds of formula (20) by reaction of approximately 1 mol equivalent of a compound of formula

(54)   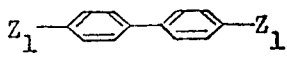

with approximately 1 mol equivalent of a compound of formula

(61)   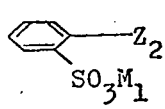

and approximately 1 mol equivalent of a compound of formula

(62)   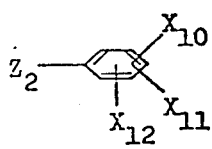

Thus, for example dialdehydes of formula

(63)   O=CH—⟨◯⟩—⟨◯⟩—CH=O can be reacted with monofunctional compounds of formula

(64)   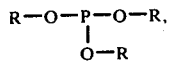

or

(65)   V—A or monoaldehydes of formula

(66)   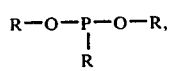

or

(67)   HOC—A can be reacted with bifunctional compounds of formula

(68)   V—⟨◯⟩—⟨◯⟩—V wherein Y, M and A have the indicated significance and V denotes a phosphorus-containing substituent of formulae (28 to 30).

The phosphorus compounds of formulae (64), (65) and (68) which are here required as starting substances are obtained in a manner which is in itself known, by reacting halogenomethyl compounds, preferably chloromethyl or bromomethyl compounds, of formula

(69)   A—CH$_2$—Halogen ,

(70)   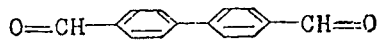 bzw. or

(71)   Halogen-CH$_2$—⟨◯⟩—⟨◯⟩—CH$_2$-Halogen with phosphorus compounds of the formulae

(72)   R—O—P—O—R,
              |
              O—R

(73)   R—O—P—O—R,
              |
              R

(74)   R—P—R
         |
         R or

(75)   R—P—OR
         |
         R

In these formulae, R has the indicated significance, with radicals R bonded to oxygen preferably being lower alkyl groups, whilst radicals R bonded directly to phosphorus are preferably aryl radicals such as benzene radicals. The phosphorus compounds of formulae (64), (65) or (68) can also be obtained by reaction of halogenomethyl compounds, preferably chloromethyl or bromomethyl compounds, of formulae (69), (70) or (71) with p-chlorodiphenylphosphine and subsequent reaction with an alcohol of formula R-OH (significance of R as defined above), for example with methanol or with water.

Possible methods for the manufacture of compounds according to formula (2) are especially those of the above-mentioned process variants according to which approximately 1 mol equivalent of a compound of formula

(76) 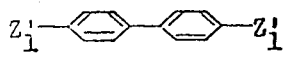

is reacted with approximately one mol equivalent each of a compound of formula

(66) 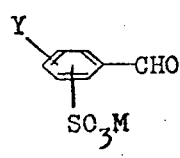

and

A—CHO     (67)

wherein Y, M and A have the abovementioned significance and $Z_1'$ denotes a grouping of formulae

(27) 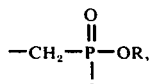

(28) 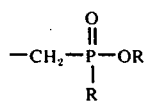

(29) 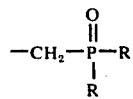

and

(30) 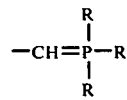

wherein R represents an optionally substituted alkyl, cycloalkyl, aryl or aralkyl radical.

A variant of particular practical importance consists of using, as diphenyl components according to formula (54), those which correspond to the formula

(77) 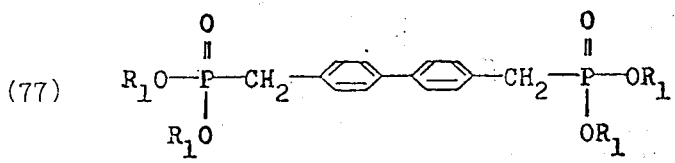

wherein $R_1$ denotes an alkyl group with 1 to 6 carbon atoms.

The manufacturing process is advantageously carried out in inert solvents. As examples thereof, hydrocarbons such as toluene and xylene or alcohols such as methanol, ethanol, isopropanol, butanol, glycols, glycol-ethers such as 2-methoxyethanol, hexanols, cyclohexanol and cyclooctanol, and also ethers such as diisopropyl ether, tetrahydrofurane and dioxane as well as dimethylsulphoxide, formamide and N-methylpyrrolidone may be mentioned. Polar organic solvents such as dimethylformamide and dimethylsulphoxide are particularly suitable. Some of the reactions can also be carried out in aqueous solution.

The temperature at which the reaction is carried out can vary within wide limits. It is determined ($\alpha$) by the stability of the solvent used towards the reagents, especially towards the strongly basic alkali compounds, ($\beta$) by the reactivity of the condensation partners and ($\gamma$) by the activity of the combination of solvent-base as a condensation agent.

According to this, temperatures between about 10° and 100°C are in general used in practice, especially if dimethylformamide or dimethylsulphoxide are used as the solvent. The preferred temperature range lies at 20° to 60°C. Under certain circumstances higher temperatures can however also be used, if this is desired for reasons of time saving or if a less active, but on the other hand cheaper, condensation agent is to be employed: fundamentally, reaction temperatures within the range of 10° to 180°C are hence also possible.

Possible strongly basic alkali compounds are above all the hydroxides, amides and alcoholates (preferably those of primary alcohols containing 1 to 4 carbon atoms) of the alkali metals, with those of lithium, sodium and potassium being of predominant interest for economic reasons. However, fundamentally, and in special cases, alkali sulphides and alkali carbonates, arylalkali compounds such as for example phenyllithium, or strongly basic amines (including ammonium bases, for example trialkylammonium hydroxides) can also be used with success.

Mixtures of asymmetrically substituted bis-stilbene compounds according to formula (16) and the two corresponding symmetrically substituted bis-stilbenes are in most cases first obtained according to the process described above, as a result of competing reaction of the three reagents. The separation of these components can be carried out on the basis of their different solution behaviour in water, with the water-insoluble compound being separated off by filtration. The water-soluble compounds remaining in the filtrate can then be separated on the basis of their different solubility in water.

The new compounds defined above possess a more or less pronounced fluorescence in the dissolved or finely divided state. They can be used for the optical brightening of the most diverse synthetic, semi-synthetic or natural organic materials or substances which contain such organic materials.

The following groups of organic materials, to the extent that optical brightening of these is relevant, may be mentioned as examples of the above, without any restriction thereof being intended to be expressed by the survey given below:

I. Synthetic organic high molecular materials.
 a. Polymerisation products based on organic compounds containing at least one polymerisable carbon-carbon double bond, that is to say their hompolymers or copolymers as well as their after-treatment products such as for example cross-linking, grafting or degradation products, polymer dilutions, products obtained by modification of reactive groups and the like, for example polymers based on α,β-unsaturated carboxylic acids or derivatives of such carboxylic acids, especially of acrylic compounds (such as for example acrylic esters, acrylic acids, acrylonitrile, acrylamides and their derivatives or their methacrylic analogues), or polymers based on vinyl and vinylidene compounds (such as for example vinyl alcohol),
 b. polymerisation products such as are for example obtainable by ring opening, for example polyamides of the polycaprolactam type, and also polymers which are obtainable both via polyaddition and also polycondensation, such as polyethers or polyacetals,
 c. polycondensation products or precondensates based on bifunctional or polyfunctional compounds possessing groups capable of condensation, their homocondensation and co-condensation products as well as products of after-treatment, such as for example polyamides (for example hexamethylenediamine adipate), maleate resins, melamine resins, their precondensates and analogues, polycarbonates or silicones, and
 d. polyaddition products such as polyurethanes (cross-linked and uncrosslinked) or epoxide resins.

II. Semi-synthetic organic materials such as for example cellulose esters of various degrees of esterfication (acetate or triacetate) or cellulose ethers, regenerated cellulose (viscose or cuprammonium cellulose) or their after-treatment products, or casein plastics.

III. Natural organic materials of animal or vegetable origin, for example based on cellulose or proteins such as cotton, wool, linen, silk, natural lacquer resins, starch or casein.

The organic materials to be optically brightened can belong to the most diverse states of processing (raw materials, semi-finished goods or finished goods). They can on the other hand be in the form of structures of the most diverse shape, that is to say for example predominantly three-dimensional articles such as sheets, profiles, injection mouldings, various machined articles, chips, granules or foams, and also predominantly two-dimensional articles such as films, foils, lacquers, coatings, impregnations or coverings or predominantly one-dimensional articles such as filaments, fibres, flocks or wires. The said materials can on the other hand also be in unshaped states, in the most diverse homogeneous or inhomogeneous forms of distribution, such as for example powders, solutions, emulsions, dispersions, latices, pastes or waxes and the like.

Fibre materials can for example be in the form of endless filaments (stretched or unstretched), staple fibres, flock, hanks, textile filaments, yarns, threads, fibre fleeces, felts, waddings, flocked structures or textile woven fabrics or textile laminates, knitted fabrics as well as papers, cardboards or paper compositions and the like.

The compounds to be used according to the invention are, inter alia, of significance for the treatment of organic textile materials, especially woven textile fabrics. Where fibres, which can be in the form of staple fibres or endless filaments, hanks, woven fabrics, knitted fabrics, fleeces, flocked substrates or laminates, are to be optically brightened in accordance with the invention, this is advantageously done in an aqueous medium, in which the compounds in question are present in a finely divided form (suspensions, or solutions where appropriate). Dispersing agents, stabilisers, wetting agents and further auxiliary agents can optionally be added during the treatment. Depending on the type of brightener compound used, it can prove advantageous preferably to work in a neutral or alkaline or acid bath. The treatment is customarily carried out at temperatures of about 20° to 140°C, for example at the boiling point of the bath or near this (about 90°C). For the finishing of textile substrates in accordance with the invention it is also possible to use solutions or emulsions in organic solvents, as is practised in the dyeing industry in so-called solvent dyeing (padder-thermofixing application, or exhaustion dyeing process in dyeing machines).

The new optical brighteners according to the present invention can furthermore be added to the materials, or incorporated into the materials, before or during their shaping. Thus they can for example be added to the compression moulding composition or injection moulding composition in the manufacture of films, foils of mouldings.

Where the shaping of fully synthetic or semi-synthetic organic material is carried out by spinning processes or via spinning compositions, the optical brighteners can be applied in accordance with the following processes: addition to the starting substances (for example monomers) or intermediate products (for example precondensates or prepolymers), that is to say before or during the polymerisation, polycondensation or polyaddition, powdering of polymer chips or granules for spinning compositions, bath dyeing of polymer chips or granules for spinning compositions, metered addition to spinning melts or spinning solutions, or application to spinning tows before stretching.

The new optical brighteners according to the present invention can for example also be employed in the following use forms:

a. Mixed with dyestuffs (shading) or pigments (for example white pigments) or as an additive to dyebaths or printing, etching or reserve pastes. Furthermore also for the after-treatment of dyeings, prints or discharge prints b. mixed with so-called "carriers", wetting agents, plasticisers, swelling agents, antioxidants, light protection agents, heat stabilisers or chemical bleaching agents (bleaching bath additives), c. mixed with crosslinking agents or dressings (for example starch or synthetic dressings), and also in combination with the most diverse textile finishing processes, especially synthetic resin finishes (for example creaseproof finishes such as "wash and wear", "permanent press" or "no-iron"), and also flameproof, soft handle or antistatic finishes or antimicrobial finishes, d. incorporation of the optical brighteners into polymeric carrier materials (polymerisation, polycondensation or polyaddition products) in a dissolved or dispersed form, for example for use in coating or impregnating agents or binders (solutions, dispersions or emulsions) for textiles, fleeces, paper or leather, e. as additives to so-called "master batches", f. as additives to the most diverse industrial products in order to make these more marketable (for example improving the appearance of soaps, detergents, pigments and the like), g. in combination with other substances having an optical brightening effect, h. in spinning bath preparations, that is to say as additives to spinning baths such as are used for improving the slip for the further processing of synthetic fibres, or from a special bath before the esterification of the fibre, and i. as scintillators for various purposes of a photographic nature, such as for example for electro-photographic reproduction or super-sensitisation.

If the brightening process is combined with textile treatment or finishing methods, the combined treatment can in many cases be advantageously carried out with the aid of appropriate stable preparations which contain the optically brightening compounds in such concentration that the desired brightening effect is achieved.

In certain cases the brighteners are brought to full effect by an after-treatment. This can for example be a chemical treatment (for example acid treatment), a thermal treatment (for example heat) or a combined chemical/thermal treatment. Thus for example an appropriate procedure to follow when optically brightening a series of fibre substrates with the brighteners according to the invention is to impregnate these fibres with the aqueous dispersions or solutions of the brighteners at temperatures below 75°C, for example at room temperature, and subject them to a dry heat treatment at temperatures above 100°C, it being generally advisable furthermore to dry the fibre material beforehand at moderately elevated temperature, for example at not less than 60°C up to about 130°C. The heat treatment in the dry state is then advantageously carried out at temperatures between 120° and 200°C, for example by warming in a drying chamber, by ironing in the indicated temperature range or also by treatment wth dry superheated steam. The drying and dry heat treatment can also be carried out in immediate succession or be combined in a single working step.

The amount of the new optical brighteners to be used according to the invention, relative to the material to be opticaly brightened, can vary within wide limits. A distinct and lasting effect can already be achieved with very small amounts, in certain cases for example amounts of 0.0001 per cent by weight. It is however also possible to use amounts of up to about 0.8 per cent by weight and above. In some cases for instance amounts of about 0.001% by weight, may suffice to produce a distinct and durable effect, though it is also possible to use amounts of up to about 0.5% by weight or more. For most practical purposes an amount ranging from 0.01 to 0.2% by weight will be preferred. For most practical purposes amounts between 0.0005 and 0.5 per cent by weight are preferably of interest.

The new optical brighteners are also particularly suitable for use as additives to washing liquors or to commercial and domestic detergents, and they can be added in various ways. An appropriate addition to washing liquors is in the form of their solutions in water or organic solvents or also in a finely divided form as aqueous dispersions. They are advantageously added to domestic or commercial detergents in any stage of the manufacturing process of the detergents, for example the so-called "slurry" before atomising the washing powder, or during the preparation of liquid detergent combinations. They can be added both in the form of a solution or dispersion in water or other solvents and as a dry brightening powder, without auxiliary agents. The brighteners can for example be mixed, kneaded or ground with the detergent substances and added to the finished washing powder in this way. They can however also be sprayed, in a dissolved or pre-dispersed form, onto the finished detergent.

Possible detergents are the known mixtures of detergent substances such as for example soap in the form of chips and powder, Syndet (soluble salts of sulphonates of higher fatty alcohols), higher and/or multiple alkyl-substituted arylsulphonic acids, sulphocarboxylic acid esters of medium to higher alcohols, fatty acid acylaminoalkyl or -aminoaryl-glycerinesulphonates, phosphoric acid esters of fatty alcohols and the like. Possible so-called "builders" are for example alkali polyphosphates and polymetaphosphates, alkali pyrophosphates, alkali salts of carboxymethyl cellulose and other soil redeposition inhibitors, and also alkali silicates, alkali carbonates, alkali borates, alkali perborates, nitrilotriacetic acid, ethylenediaminotetraacetic acid, and foam stabilisers such as alkanolamides of higher fatty acids. The following can furthermore be present therein: antistatic agents, re-greasing skin protection agents such as lanoline, and also enzymes, anti-microbial agents, perfumes and dyestyffs.

The new optical brighteners possess the particular advantage that they are also effective in the presence of active chlorine donors such as for example hypochlorite, and that they can without significant loss of effects be employed in washing liquors containing non-ionic detergents, for example alkylphenolpolyglycol ethers.

The compounds according to the invention are added in amounts of 0.005 – 1% or above, relative to the weight of the liquid or powder-form finished detergent. Washing liquors which contain the indicated amounts of the optical brighteners claimed impart a brilliant appearance in daylight when used for washing textiles of cellulose fibres, polyamide fibres, cellulose fibres with a high quality finish and the like.

The washing treatment is for example carried out as follows: the textiles indicated are treated for 1 to 30 minutes at 20° to 100°C in a washing liquor which contains 1 to 10 g/kg of a built-up composite detergent and 0.05 to 1%, relative to the weight of the detergent, of the brighteners claimed. The liquor ratio can be 1:3 to 1:50. After washing, the material is rinsed and dried in the customary manner. The washing liquor can contain 0.2 g/l of active chlorine (for example as hypochlorite) or 0.1 to 2 g/l of sodium perborate as a bleaching additive.

In the examples the parts, unless otherwise stated, are always parts by weight and the percentages always percentages by weight. Unless otherwise noted, melting points and boiling points are uncorrected.

Within the framework of the present invention it is also possible without difficulty — depending on the special technical requirements in use — to employ the new compounds described mixed with the corresponding compounds of symmetrical structure, obtainable from the competing reaction of the manufacturing process, for the purpose of optical brightening. This means that in practical application it is also possible — depending on the end use — to dispense with a separation of the competing reaction products. Where appropriate, the symmetrical water-insoluble compound can be separated off, whilst the water-soluble compounds are used as a mixture for the purpose of optical brightening.

Where appropriate it is possible, in order to reduce the proportion of the symmetrical water-insoluble compound in the reaction mixture, to conduct the reaction in such a way that per mol equivalent of the bifunctional reaction component employed a total of about two mol equivalents of monofunctional reaction components are employed, it being possible for the ratio of component containing sulphone groups to the component free of sulphone groups to lie roughly in the molar ratio of between 1:1 and 10:1.

EXAMPLE 1

A solution of 32.7 g of the sodium salt of benzaldehyde-2-sulphonic acid (containing about 70% of free sulphonic acid) and 22.7 g of 4,4′-bis-(diethoxyphosphonomethyl)-diphenyl in 50 ml of anhydrous dimethylformamide (a small insoluble residue is filtered off) is stirred dropwise at 40° – 50°C within 40 minutes into a suspension of 60 g of potassium tertiary butylate in 125 ml of anhydrous dimethylformamide, whereupon a slightly exothermic reaction produces a red-brown suspension. The reaction mixture is stirred on for 1 hour at 40° – 50°C and then poured into 2.5 liters of cold water. The resulting light-yellow, turbid solution is heated to the boil, filtered and the hot filtrate mixed with 375 g of sodium chloride. On cooling, the light-yellow product crystallizes out; it is recrystallized twice from a mixture of 900 ml of water and 90 ml of glacial acetic acid with addition of 18 g of sodium chloride, once from a mixture of 100 ml of dimethylformamide and 1 liter of water with addition of 150 g of sodium chloride and twice from 900 and 500 ml of ethanol. Yield: About 4.0 g (= 14.2% of theory) of the compound of the formula triethylphosphite is distilled off under atmospheric pressure, the batch cooled to 120°C, mixed with ½ liter of toluene, and cooled to room temperature, whereupon the product crystallizes out and is filtered off. After recrystallization from toluene there are obtained 361.5 g (= 66.3% of theory) of 4,4′-bis-(diethoxyphosphonomethyl)-diphenyl of the formula

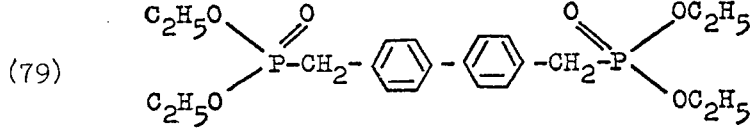
(79)

as a white crystal powder melting at 108° – 110°C.

EXAMPLE 2

In a vessel from which the air has been displaced by nitrogen a well-stirred suspension of 126.5 g of powdered potassium hydroxide (containing about 89% of KOH) in 500 ml of anhydrous dimethylformamide is slowly mixed with a homogeneous mixture of 113.5 g of 4,4′-bis-(diethoxyphosphonomethyl)-diphenyl and 129 g of the sodium salt of benzaldehyde-2-sulphonic acid containing about 86% of free sulphonic acid. The temperature rises gradually to 45°C and the batch is maintained at 40 to 45°C by ice cooling, and then stirred on for another 3 hours at 40° to 45°C. The reaction mixture is then poured into 3.5 liters of distilled water of about 70°C. The resulting, slightly turbid solution is mixed with 1.5 kg of sodium chloride and about 1.5 kg of ice, whereupon the temperature of the pale-yellow suspension drops to about 25°C. The pH value of the suspension is adjusted to about 7 with 37% hydrochloric acid. The batch is then stirred for 1 hour at room temperature, suction-filtered and the product washed with 23% sodium chloride solution and dried, to yield about 158 g of crude product which contains 21% of sodium chloride and 125 g of the compound of the formula (78), corresponding to a yield of 89% of the theoretical. Recrystallization of the moist suction filter cake from ethanol furnishes about 117 g of pure product containing 13% of sodium chloride, corresponding to a pure yield of 72% of the theoretical. The product of the formula (78) can be obtained in salt-free form by further recrystallization from alcohol.

Analysis: $C_{28}H_{20}Na_2O_6S_2$: Calculated: C, 59.78; H, 3.58; S, 11.40%. Found: C, 59.62; H, 3.54; S, 11.19%.

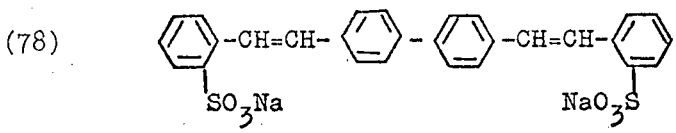
(78)

in light yellow, fine needles.

The 4,4′-bis-(diethoxyphosphonomethyl)-diphenyl used as starting material is accessible by the following route:

420 Grams of triethylphosphite are mixed at 142° – 146°C within 1 hour with 301 g of 4,4′-bis-chloromethyldiphenyl in 1200 ml of xylene. The reaction mixture is refluxed for 20 hours and the solvent is then distilled off under atmospheric pressure. Then another 410 ml of triethylphosphite are added and the reaction mixture is refluxed for another 20 hours. The excess When, instead of 113.5 g of 4,4′-bis-(diethoxyphosphonomethyl)-diphenyl, 99.6 g of 4,4′-bis-(dimethoxyphosphonomethyl)-diphenyl and 116 g of the sodium salt of benzaldehyde-2-sulphonic acid (containing about 88% of free sulphonic acid) are used and the identical procedure is adopted, but the reaction time used is 5 hours, there are obtained about 163 g of crude product containing 24.5% of sodium chloride, corresponding to a yield of 87% of theoretical. When the crude product is dissolved in 1600 ml of boiling distilled water, filtered clear, rinsed with 400 ml of boiling distilled water, the clear filtrate is mixed with 400 g of sodium chloride and the whole is cooled, suctioned and the crystalline product formed is dried, there are obtained about 147 g of the product of the formula (78) containing 18% of sodium chloride, corresponding to a pure yield of 86% of theory.

When in this process potassium hydroxide is replaced by an equivalent quantity of sodium hydroxide containing about 98% of NaOH, the product of the formula (78) is obtained in a crude yield of 73% and in a pure yield of 70% of the theoretical. If potassium hydroxide or sodium hydroxide is replaced by sodium methylate, good results are also obtained. Finally, the solvent used may be dimethylsulphoxide instead of dimethylformamide. In this case the condensing agent may be a concentrated aqueous solution of potassium hydroxide (for example of 67% strength), the water content of the reaction mixture then amounting to about 8%.

The 4,4′-bis-(dimethoxyphosphonomethyl)-diphenyl used above may be prepared thus:

A mixture of 261 g of 4,4′-bis-(chloromethyl)-diphenyl and 372 g of trimethylphosphite is stirred at the reflux, temperature (117° – 119°C) until methylchloride is no longer being evolved, which takes about 8 hours. The excess trimethylphosphite is distilled off under vacuum, and the clear, colourless solution is diluted with 600 ml of toluene and allowed to crystallize. After suctioning, washing with a small quantity of toluene and drying, there are obtained 358 g (=90% of theory) of bis-(dimethoxyphosphonomethyl)-diphenyl of the formula A strong current of hydrogen chloric gas is introduced into a vigorously stirred mixture of 1542 g of biphenyl, 671 g of paraformaldehyde (of 98% strength), 927 g of zinc chloride (of 98% strength) and 2 liters of cyclohexane, while maintaining by external cooling a temperature of 50°C until all reactants have dissolved and then for 24 hours at 30°C. The resulting bis-chloromethyl-diphenyl crystallizes out continuously. After suctioning at 15°C, washing with cyclohexane and water and drying at 70°C under vacuum there are obtained 1580 g (= 63% of theory) of bis-chloromethyl-diphenyl as a colourless crystalline powder melting at 132° – 135°C.

EXAMPLE 3

113.5 Grams of 4,4′-bis-(diethoxyphosphonomethyl)-diphenyl and 222 g of the disodium salt of benzaldehyde-2,4-disulphonic acid (containing about 70% of free acid) in 800 ml of anhydrous dimethylformamide and 126 g of powdered potassium hydroxide are reacted as described in Example 2. After a reaction time of one hour the thick reaction mixture is poured into 1.4 liter of distilled water heated at about 80°C, the turbid solution is filtered until clear, and the filtrate is cooled to 15°C and mixed with 5 liters of ethanol. The resulting crystalline product is suctioned off and dried under vacuum. Yield: about 113 g (= 59.3% of theory, referred to the tetrasodium salt).

Recrystallization from aqueous methanol, conversion into the free tetrasulphonic acid by means of an ion

(80) 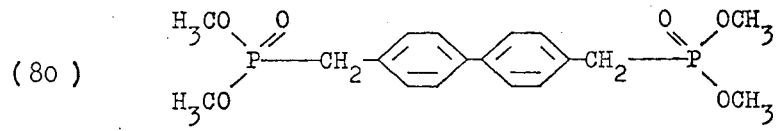

in colourless crystals melting at 129° – 130°C. An analytically pure product obtained by recrystallization from toluene melts at 130° – 131°C.

exchange resin and neutralization with sodium hydroxide solution furnishes the pure tetrasodium salt of the formula

(81) 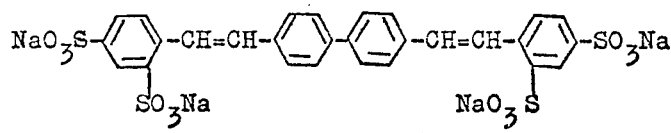

$C_{18}H_{24}O_6P_2$ (molecular weight 398.33): Calculated: C, 54.28; H, 6.07; P, 15.55%. Found: C, 54.53; H, 6.02; P, 15.39%.

When trimethylphosphite is replaced by an equivalent quantity of triethylphosphite, there is obtained at a final temperature of 160°C a yield of 89% of the theoretical of bis-(diethoxyphosphonomethyl)-diphenyl of the formula (79) in colourless crystals melting at 107° – 109°C. A specimen recrystallized from toluene melts at 108° – 110°C.

$C_{22}H_{32}P_2O_6$ (molecular weight 454.44) Calculated: C, 58.15; H, 7.10; P, 13.63%. Found: C, 57.89; H, 7.22; P, 13.64%.

The 4,4′-bis-(chloromethyl)-diphenyl used as starting material may be prepared thus:

in light-yellow, fine needles.

Analysis: $C_{28}H_{18}Na_4O_{12}S_4$: Calculated: C, 43.87; H, 2.37; S, 16.73%. Found: C, 43.39; H, 2.67; S, 16.17%.

The bis-stilbene compounds of the formula

(82) 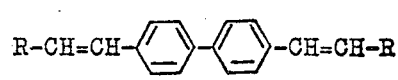

listed in the following Table may be prepared in a similar manner.

The sodium salt of 5-formyl-2-methylbenzenesulphonic acid used as starting material for the bis-stilbene compound of the formula (88) is obtained by sulphonating 4-methylbenzaldehyde with oleum containing 66% of SO₃ and purification via the barium salt. In a similar manner the sodium salt of 5-formyl-2methoxy-benzenesulphonic acid, used as starting material for the bis-stilbene compound of the formula (89), is obtained from 4-methoxybenzaldehyde.

The aldehyde

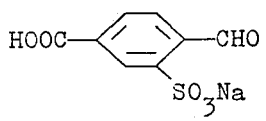

| Nº | R | Colour of powder |
|---|---|---|
| 83 | ⌬ with SO₃Na (top) and SO₃Na (bottom) | light yellow |
| 84 | ⌬ with Cl and SO₃Na | light yellow |
| 85 | ⌬ with C≡N and SO₃Na | yellow |
| 86 | ⌬ with COONa and SO₃Na | greenish yellow |
| 87 | ⌬ with SO₃Na | pale yellow |
| 88 | ⌬ with CH₃ and SO₃Na | pale greenish yellow |
| 89 | ⌬ with OCH₃ and SO₃Na | '' |
| 90 | ⌬ with SO₃Na | light beige |
| 91 | ⌬ with SO₃Na and SO₃Na | pale yellow | as used in preparing compound (86)) was prepared according methods per se by sulfonation of p-toluene-carboxylic acid and oxidation of the methyl group with $MnO_2$.

The aldehyde

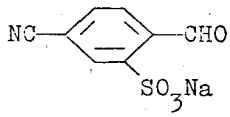

as used in preparing compound (85)) was obtained by oxidation of 4,4'-dicyano-stilbene-2,2'-disulfonic acid. The latter was prepared by diazotation of 4,4'-diamino-stilbene-2,2'-disulfonic acid and reaction according to Sandmeyer (KCN/copper-II-ions).

EXAMPLE 4

200 Grams of the compound of the formula (78) in a mixture of 1 liter of anhydrous chlorobenzene, 500 ml of thionylchloride and 1 ml of dimethylformamide are heated with stirring within 35 minutes to 95°C and then stirred for 20 hours at 95°–100°C. The batch is then cooled, the product which has crystallized out is suctioned off and recrystallized from 2 liters of anhydrous chlorobenzene.

Yield: about 117.3 g (= 60.4% of theory) of the compound of the formula (92)

in shiny, yellow, small flakes, melting at 236° – 237°C.

Analysis: $C_{28}H_{20}Cl_2O_4S_2$: Calculated: C, 60.54; H, 3.63; Cl, 12.76%. Found: C, 60.57; H, 3.92; Cl, 12.63%.

In a similar manner the sulphochloride of the formula (93)

is obtained in small yellow, shiny flakes melting above 300°C.

Likewise, in a similar manner the compounds of the formulae (81), (87) and (88) furnishes the sulpho-chloride of the formula (94)

(95)

(96)

melting above 300°C.

EXAMPLE 5

11.1 Grams of the compound of the formula (93) in 150 ml of dimethylformamide are heated with stirring for 2 hours at 145° to 150°C. The batch is then cooled to 80°C, 150 ml of ethanol are added, the whole is cooled to 5°C and the crystalline product formed is suctioned off, recrystallized from 400 ml of dimethylformamide and dried under vacuum.

Yield: 4.5 g of the compound of the formula (97.)

Analysis: $C_{32}H_{36}N_2O_6S_2$: Calculated: C, 63.14; H, 5.96; N, 4.60; S, 10.53%. Found: C, 63.02; H, 5.93; N, 4.47; S, 10.54%.

When the compound of the formula (97) is dissolved in aqueous dimethylformamide and 30% sodium hydroxide is added to the hot solution, the sodium salt of the formula (90) is obtained.

Analysis: $C_{28}H_{20}Na_2O_6S_2$: Calculated: C, 59.78; H, 3.58; S, 11.40% Found: C, 59.55; H, 3.82; S, 11.09%.

When the compound of the formula (78) is dissolved in water and barium chloride or calcium chloride is added, the corresponding barium and calcium salt respectively is obtained.

When a solution of the compound of the formula (78) is treated with a strongly acid ion exchange resin, a solution of the free sulfonic acid is obtained which can be isolated by evaporation. The corresponding amine salts can be obtained by neutralization with amines, for example by means of diethanolamine, the diethanolammonium salt is obtained.

When instead of ammonia dimethylamine is introduced for 6 hours at 60° to 65°C, and the product is recrystallized from dimethylformamide, there are obtained 20.7 g of the compound of the formula (99)

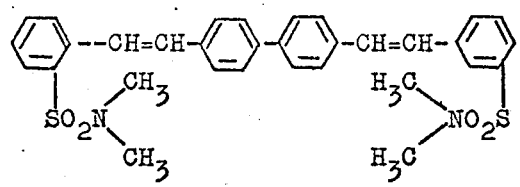

in small light-yellow, shiny flakes melting at 280° to 281°C.

When, instead of injecting dimethylamine, 42 g of diethanolamine are dropped in at 60° to 65°C, the batch is then heated for 1 hour at 120° to 125°C and the product is recrystallized from dimethylformamide+ethanol with addition of active carbon, there are obtained 8.0 g of the compound of the formula

EXAMPLE 6

27.8 Grams of the compound of the formula (92) are dissolved with stirring at 120°C in 300 ml of anhydrous chlorobenzene and then a moderate current of dry ammonia is injected for 30 hours. After cooling, the resulting crystalline product is suctioned off and twice recrystallized from aqueous dimethylformamide.

Yield: 16.2 g of the compound of the formula (100)

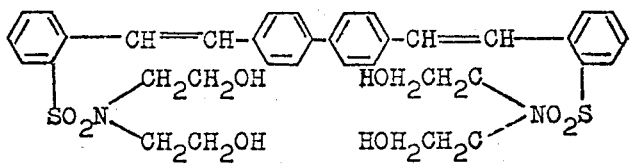

in pale yellow fine needles melting at 232° to 233°C.

EXAMPLE 7

13.9 Grams of the compound of the formula (92) are introduced into 200 ml of n-octylamine and the whole is heated with stirring for 45 minutes to 75° to 80°C. The pale yellow solution is cooled, 100 ml of methanol are added and the precipitated product suctioned off and recrystallized twice from chlorobenzene with addition of bleaching earth. Yield: 10.4 g (= 56.3% of theory) of the compound of the formula (98)

in fine, pale yellow flakes melting at 280.5° – 282°C.

Analysis: $C_{28}H_{24}N_2O_4S_2$: Calculated: C, 65.10; H, 4.68; N, 5.42; S, 12.41%. Found: C, 64.92; H, 4.69; N, 5.15; S, 12.35%.

(101)

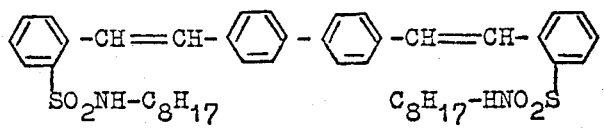

form of a colourless crystal powder melting at 143.5–144°C.
The bis-stilbene compounds of the formula (82) listed in the following Table may be prepared in a similar manner:
| NO. | R | Melting point °C |
|---|---|---|
| 102 | 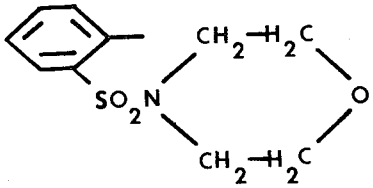 | 256 – 257 |
| 103 | 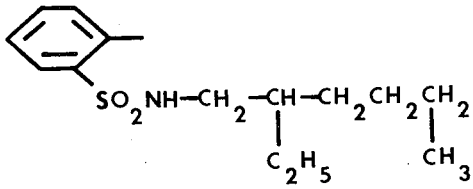 | 144.5 – 145 |
| 104 | 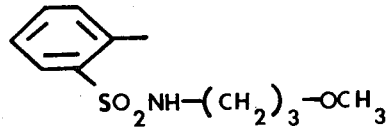 | 148.5 – 149.5 |
| 105 | 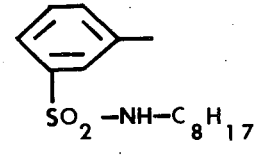 | 245 – 246 |
| 106 | 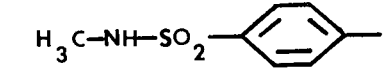 | above 300 |
| 107 | 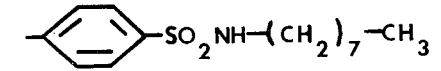 | above 300 |
| 108 | 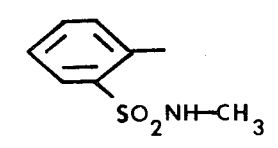 | 234 – 235 |

| No. | R | Melting point °C |
|---|---|---|
| 109 | 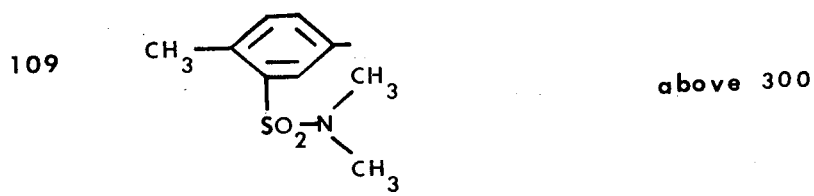 | above 300 |
| 110 | 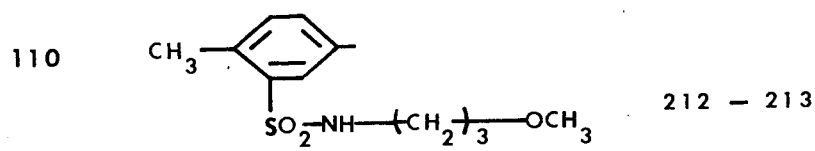 | 212 – 213 |
| 111 | 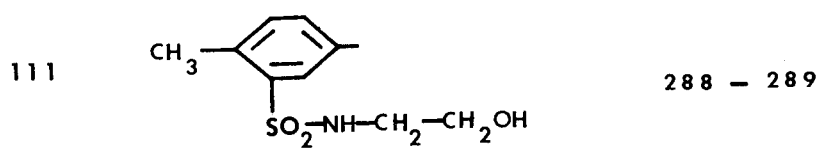 | 288 – 289 |
| 112 | 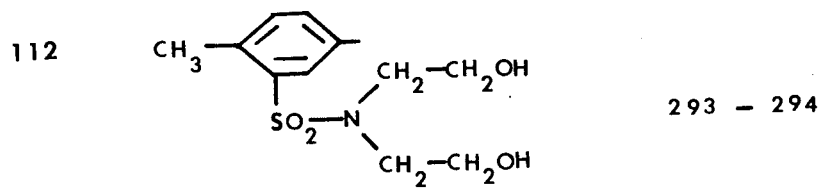 | 293 – 294 |
| 113 | 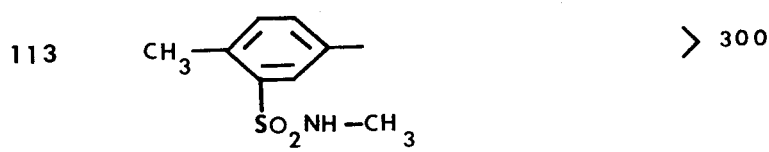 | > 300 |
| 113a | 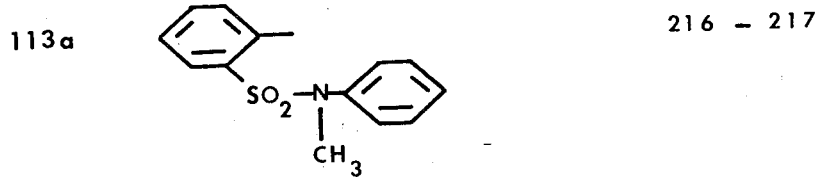 | 216 – 217 |

EXAMPLE 8

27.8 Grams of the compound of the formula (92) are slowly stirred at room temperature into a solution of 40.8 g of 3-dimethylamino-1-propylamine in 300 ml of ethanol. The mixture is then stirred for 5 hours at 55° to 60°C, the crystalline precipitate suctioned off, washed with water and ethanol and dried under vacuum. Yield: 33.5 g (= 97.7% of theory) of the compound of the formula (114)
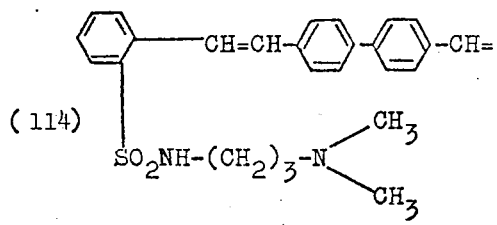
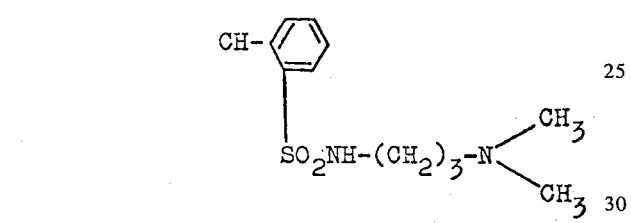

After two recrystallizations from aqueous dimethylformamide with the aid of active carbon there are obtained 25.0 g (= 72.8% of theory) of yellow platelets melting at 164.5°–165.5°C.

Analysis: $C_{38}H_{46}N_4O_4S_2$: Calculated: C, 66.44; H, 6.75; N, 8.16; S, 9.34%. Found: C, 66.25; H, 6.78; N, 7.89; S, 9.41%.

A mixture of 13.7 g of the compound of the formula (114) and 15 ml of dimethylsulphate in 1.5 liters of methanol is refluxed for 4 hours, then 700 ml of methanol are distilled off and the product of the the formula (114a)
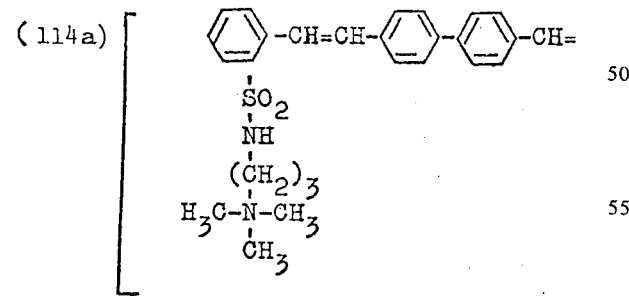
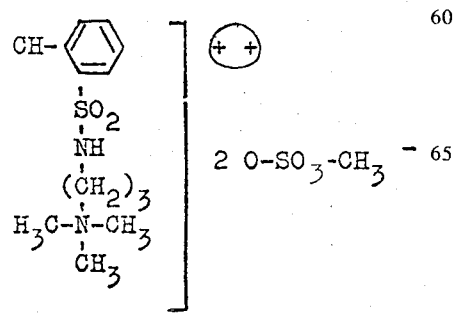

settles out in form of practically colourless crystals. After recrystallization from methanol+hexane it melts at 254° to 256°C.

In a similar manner there can be obtained from the compound of the formula (95) the compound of the formula (115)
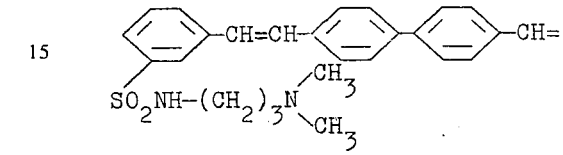
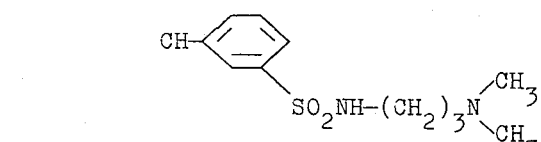

and from the latter the compound of the formula (115a)
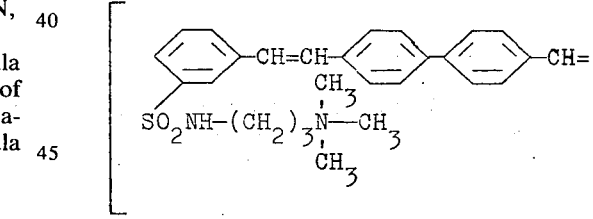
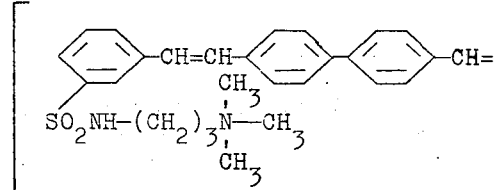
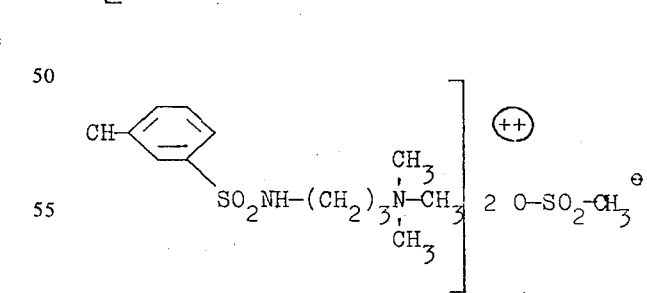
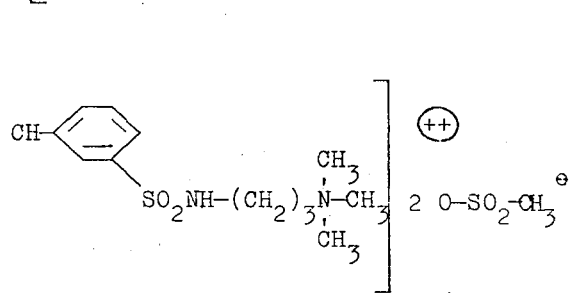

EXAMPLE 9

13.9 Grams of the compound of the formula (92) are slowly stirred at room temperature into a solution of 9.4 g of phenol in 100 ml of anhydrous pyridine. The batch is heated for 2 hours at 95° to 105°C, then cooled to 5°C, the residue filtered off and the clear filtrate is mixed with 200 ml of hexane, the precipitate suctioned off, dried, twice extracted with boiling water, again dried and recrystallized from chlorobenzene. The product is dissolved in 200 ml of dioxane, clarified by filtration, mixed with 300 ml of ethanol and 50 ml of water and allowed to crystallize, to yield 1.2 g of the compound of the formula (116) 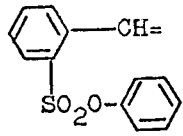

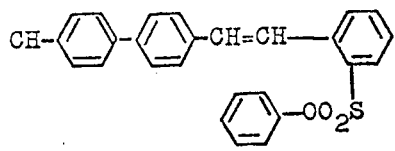

in pale yellow small needles melting at 241° to 241.5°C.
Analysis: $C_{40}H_{30}O_6S_2$: Calculated: C, 71.62; H, 4.51; S, 9.56%. Found: C, 71.36; H, 4.72; S, 9.65%.

In a similar manner the compounds of the formulae (93) and (95) yield the corresponding para,para'- and meta,meta'-compounds, respectively.

EXAMPLE 10

20 Grams of the crude sulphochloride of the formula (94) are stirred into a mixture of 800 ml of methylcellosolve and 100 ml of 24% ammonium hydroxide solution and the whole is heated for 4 hours at 90° to 95°C. The turbid solution is clarified by filtration and mixed with 800 ml of water and 50 ml of concentrated hydrochloric acid. The precipitate is suctioned off, washed neutral with water, dried and recrystallized from aqueous dimethylformamide, to yield 1.0 g of the compound of the formula (116a) 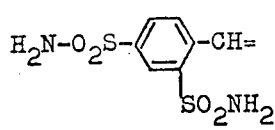

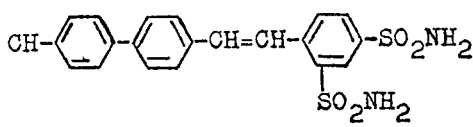

in form of small yellow flakes melting above 300°C.
Analysis: $C_{28}H_{26}N_4O_8S_4$: Calculated: C, 49.84; H, 3.88; S, 19.01%. Found: C, 49.77; H, 4.03; S, 18.92%.

EXAMPLE 11

10 Grams of the crude compound of the formula (94) are suspended with stirring in 200 ml of chlorobenzene and for 6 hours dimethylamine is injected at about 60°C. After cooling, the batch is suction-filtered and the filter residue recrystallized from dimethylformamide+ethanol or dioxane+ethanol to yield 1.9 g of the compound of the formula (117) 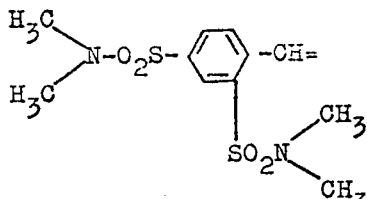

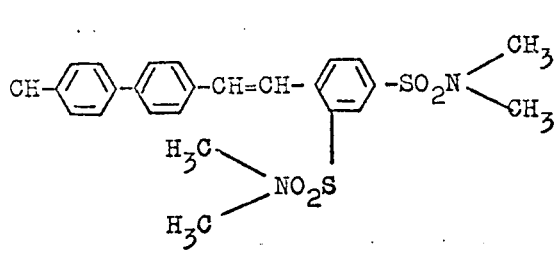

as a yellow crystal powder melting at 257.5° to 258°C.
Analysis: $C_{36}H_{42}N_4O_8S_4$: Calculated: C, 54.94; H, 5.38; S, 16.30%. Found: C, 54.68; H, 5.37; S, 16.12%.

EXAMPLE 12

10 Grams of the crude sulphochloride of the formula (94) in 200 ml of n-octylamine are stirred and heated for 3 hours at 75° to 80°C. The turbid solution is clarified by filtration cooled, mixed with a little water and 1.5 liters of methanol and the precipitate is filtered off and recrystallized from aqueous dimethylformamide. Yield: 3.9 g of the compound of the formula (118) 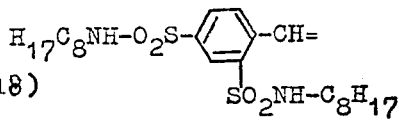

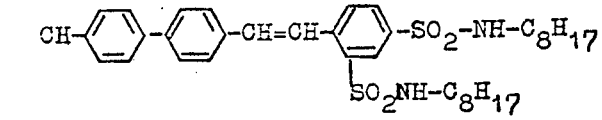

in lemon-coloured small needles melting at 255° to 256°C.
Analysis: $C_{60}H_{90}N_4O_8S_4$: Calculated: C, 64.14; H, 8.07; N, 4.99; S, 11.41%. Found: C, 64.12; H, 8.20; N, 5.00; S, 11.42%.

EXAMPLE 13

22.7 Grams of 4,4'-bis-(diethoxyphosphonomethyl)-diphenyl and 14.4 g of p-toluylaldehyde are dissolved with heating in 100 ml of anhydrous dimethylformamide. The batch is cooled to 20°C and 20g of 30% methanolic sodium methylate solution are stirred in dropwise within 15 minutes, during which the temperature rises to 48°C and a pale-yellow, thick suspension forms which is stirred on for 1 hour, diluted with 50 ml of methanol, neutralized with glacial acetic acid and the crystalline product thus formed is suctioned off and recrystallized from a mixture of 600 ml of dimethylformamide and 1200 ml of trichlorobenzene, to yield 12.2 g (= 63.3% of theory) of 4,4'-bis-(p-methyl-styryl)-diphenyl of the formula (119)
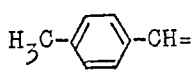
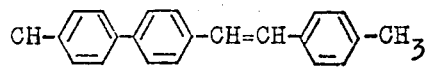

in form of shiny, pale-yellow flakes melting above 300°C.

Analysis: $C_{30}H_{26}$: Calculated: C, 93.22; H, 6.78%. Found: C, 92.98; H, 6.64%.

EXAMPLE 14

22.7 Grams of 4,4'-bis-(diethoxyphosphonomethyl)-diphenyl and 15.7 g of p-cyanobenzaldehyde are dissolved in 100 ml of anhydrous dimethylformamide with stirring at 40°C. Then, within 20 minutes, 20 g of 30% methanolic sodium methylate solution are dropped in so that the temperature does not rise above 50°C. The resulting orange-coloured suspension is further stirred for 5 hours at 45° to 50°C, then cooled to room temperature, the crystalline precipitate is suctioned off and the filter residue thoroughly washed with methanol and recrystallized from a mixture of 500 ml of trichlorobenzene and 250 ml of dimethylformamide, or from 500 ml of trichlorobenzene, with the aid of diatomaceous earth.

Yield: 4.2 g (= 20.6% of theory) of the compound of the formula (120)
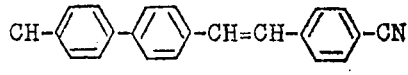

as a yellow crystal powder melting at 276° to 277°C.

Analysis: $C_{30}H_{20}N_2$: Calculated: C, 88.21; H, 4.94; N, 6.86%. Found: C, 88.08; H, 5.15; N, 6.92%.

EXAMPLE 15

A solution of 3.9 g of benzaldehyde-4-carboxylic acid methyl ester and 5.0 g of 4,4'-bis-(diethoxyphosphonomethyl)-diphenyl in 20 ml of anhydrous dimethylformamide is stirred dropwise at 40° to 50°C into a suspension of 13.2 g of potassium tertiary butylate in 200 ml of anhydrous dimethylformamide. The resulting yellow, thick suspension is stirred on for 4 hours at 40° to 45°C, cooled and the product is suctional off and recrystallized from a mixture of 1 liter of trichlorobenzene and ½ liter of dimethylformamide or from ½ liter of dimethylformamide, to yield 1.0 g (= 19.2% of theory) of the compound of the formula (121)
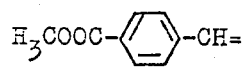
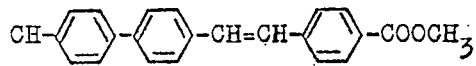

as a yellow crystal powder melting above 300°C.

A mixture of 51.6 g of the diester of the formula (121), 1.5 liters of methylcellosolve and 60 g of a 30% aqueous sodium hydroxide solution is stirred for 5 hours at 95° to 100°C, cooled, suctioned, and the resulting disodium salt is converted into the free dicarboxylic acid by acidification with aqueous hydrochloric acid; it is suctioned off, washed with water and dried.

13.4 Grams of the dicarboxylic acid in 200 ml of chlorobenzene and 0.5 ml of dimethylformamide are mixed with 20 ml of thionylchloride and heated to 95°C and then stirred for 3 hours at 95° to 100°C and cooled. The reaction product is recrystallized twice from o-dichlorobenzene, to furnish 7.3 g (= 50.3% of theory) of the compound of the formula (122)
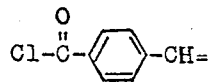
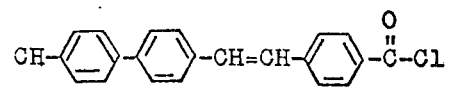

in shiny yellow flakes melting at 281° – 283°C.

Analysis: $C_{30}H_{20}O_2Cl_2$: Calculated: C, 75.54; H, 4.17; Cl, 14.67%. Found: C, 74.72; H, 4.17; Cl, 14.50%.

4.85 Grams of the compound of the formula (122) in 200 ml of chlorobenzene are stirred for 6–7 hours at 55° to 60°C while injecting anhydrous dimethylamine, then cooled, suctioned, washed with methanol and dried, to yield 4.8 g (= 96% of theory) of the compound of the formula (123)
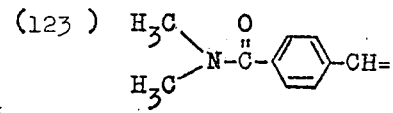
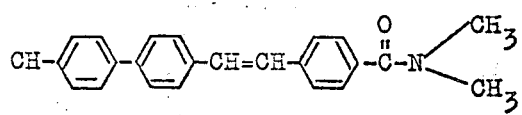

in form of bright, yellowish green, fine needles which melt above 300°C and can be purified by recrystallization from o-dichlorobenzene or dimethylformamide.

When monomethylamine is used instead of dimethylamine, the compound of the formula (124)
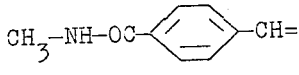
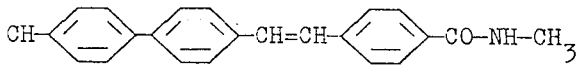

is obtained,

EXAMPLE 16

A solution of 22.7 g of 4,4'-bis-(diethoxyphosphonomethyl-diphenyl and 14.4 g of p-toluylaldehyde in 50 ml of dimethylformamide is stirred dropwise at 40° to 45°C into a suspension of 25.5 g of powdered potassium hydroxide (containing about 12% of water) in 120 ml of dimethylformamide. The resulting yellow suspension is stirred on for 2½ hours at 40° to 45°C, mixed with ½ liter of water, suctioned and the product is washed with water and methanol.

Yield: 18.1 g (= 93.8% of theory) of the compound of the formula

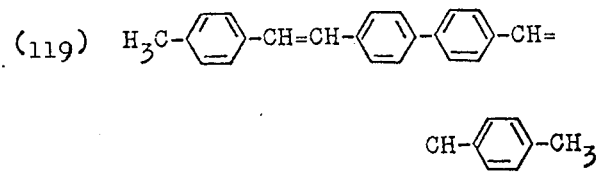

(119)

as a light-yellow powder melting above 300°C.

After recrystallization from 1.5 liters of trichlorobenzene with the aid of bleaching earth, or from a mixture of 750 ml of trichlorobenzene and 750 ml of dimethylformamide, there are obtained 8.6 g (= 44.6% of theory) of light-yellow crystals melting above 300°C.

In a similar manner the bis-stilbene compounds of the formula

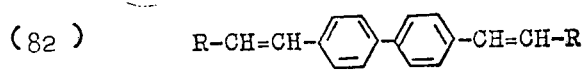

(82)

listed in the following Table are obtained. To manufacture the compound of the formula (127) the reaction mixture is acidified with aqueous hydrochloric acid on completion of the reaction.

EXAMPLE 17

A solution of 10.5 g of 4,4'-bis-formyl-diphenyl and 25.3 g of 1-diethoxyphosphonomethyl-2-cyanobenzene of the formula (129) 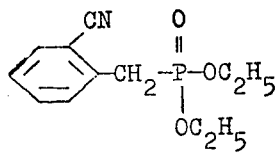

in 50 ml of dimethylformamide is dropped with stirring and exclusion of air into a suspension of 25.2 g of powdered potassium hydroxide (containing about 11% of water) in 100 ml of dimethylformamide at such a rate that the temperature does not rise above 40°C. The reaction mixture is stirred on for 3 hours at 40° to 45°C, cooled to 5°C, and 200 ml of water are dropped in. After suctioning, washing with water and methanol and drying there are obtained 18.2 g (=89.3% of theory) of 4,4'-bis-(2-cyanostyryl)-diphenyl of the formula (130) 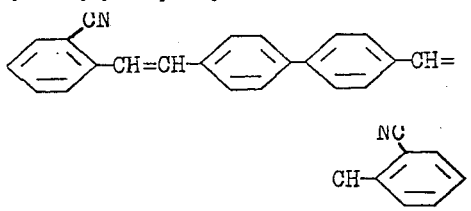

in form of fine brownish-yellow needles melting at 271°–272°C. Two recrystallizations from o-dichlorobenzene, with the aid of bleaching earth, furnish 13.5 g (=66.3% of theory) of shiny, pale yellow flakes melting at 274° to 275°C.

Analysis: $C_{30}H_{20}N_2$: Calculated: C, 88.21; H, 4.94; N, 6.86%. Found: C, 88.20; H, 5.22; N, 6.86%.

The 1-diethoxyphosphonomethyl-2-cyanobenzene of the formula (129) used as intermediate is accessible from o-tolunitrile by reaction with N-bromosuccini-

| N° | R | Melting point °C |
|---|---|---|
| 125 | ![2,4,6-trimethylphenyl] (CH₃, CH₃, CH₃ substituted phenyl) | 179.5 – 180 |
| 126 | ![3-methylphenyl] (CH₃ substituted phenyl) | 233 – 234 |
| 127 | ![4-carboxyphenyl] (COOH substituted phenyl) | above 300 |
| 128 | ![4-(N,N-dimethylsulfamoyl)phenyl] (SO₂N(CH₃)₂ substituted phenyl) | above 300 | mide to form the bromomethyl compound which is then reacted with triethylphosphite; it boils at 138° to 140°C under 0.09 mm Hg pressure.

When 1-diethoxyphosphonomethyl-2-cyano-benzene is replaced by 1-diethoxyphosphonomethyl-3-cyano-benzene the compound of the formula

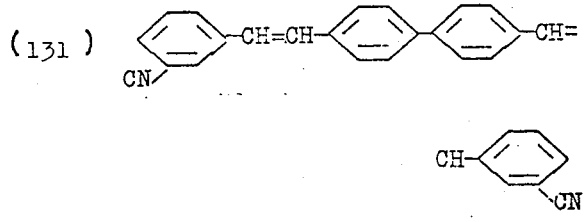

melting above 300°C is obtained.

For the manufacture of the bis-stilbene compounds of the formulae (130) and (132) the solvent used may be dimethylsulphoxide instead of dimethylformamide.

The process described in this Example is also suitable for the manufacture of the bis-stilbene compounds of the formula

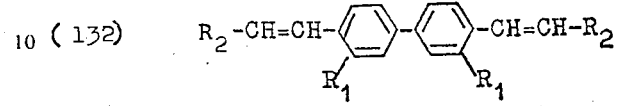

listed in the following Table:

| N° | R₁ | R₂ | Melting point °C |
|---|---|---|---|
| 133 | $-CH_3$ | ![2-cyanophenyl] | 217 – 219 |
| 134 | $OCH_3$ | ![2-cyanophenyl] | 202 – 203 |
| 135 | $-Cl$ | ![2-cyanophenyl] | 262 – 263 |
| 136 | $-SO_2-N(CH_3)_2$ | ![2-cyanophenyl] | 310 – 311 |
| 137 | $-SO_3Na$ | ![phenyl] | above 300 |
| 138 | $-CH_3$ | ![phenyl] | 171 – 172 |
| 139 | $-OCH_3$ | ![4-methylphenyl] | 204.5 – 205.5 |
| 140 | $-CH_3$ | ![3,4-dichlorophenyl] | 222 – 223 |
| 141 | $-CH_3$ | ![3-chlorophenyl] | 164 – 164.5 |
| 142 | $-CH_3$ | ![biphenyl] | 284 – 286 |
| 143 | $-CH_3$ | ![1-naphthyl] | 228 – 231 |
| 144 | $-CH_3$ | ![2-naphthyl] | 208 – 209 |

The 4,4'-bis-formyl-3,3'-dimethyl-diphenyl, used as starting material for the bis-stilbene compounds (133) and (140) to (144), is obtained by reacting diazotized tolidine with potassium cyanide/copper sulphate and reducing the resulting dinitrile by means of Raney nickel (formic acid); it melts at 108° to 109°C.

The 4,4'-bis-formyl-3,3'-dimethoxy-diphenyl, melting at 241° – 243°C, required for compounds (134) and (139), and the 4,4'-bis-formyl-3,3'-dichloro-diphenyl, melting at 220° – 222°C, required for the compound (135), are manufactured in a similar manner.

4,4'-Bis-formyl-diphenyl-3,3'-disulphonic acid is obtained through the following reaction steps:

4,4'-Dimethyl-diphenyl is sulphonated with concentrated sulphuric acid for 4–5 hours at 80°C; the resulting 4,4'-dimethyl-diphenyl-3,3'-disulphonic acid is converted with thionylchloride into the disulphonic acid dichloride melting at 192° – 193°C, which is then oxidized with chromic anhydride in acetic anhydride+λ glacial acetic acid to form the acetate chloride of the formula (145)

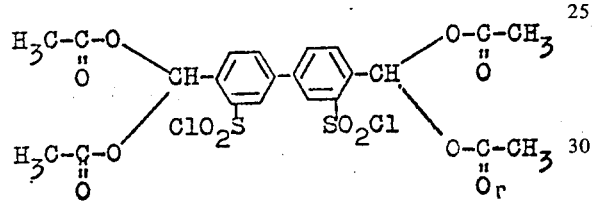

melting at 185° – 188°C, which is finally hydrolyzed in dilute hydrochloric acid to furnish the aldehydesulphonic acid.

4,4'-Bis-formyl-diphenyl-3,3'-bis-sulphonic acid dimethylamide is prepared from the sulphochloride acetate of the formula (145) by reaction with dimethylamine in chloroform and hydrolysis in dilute hydrochloric acid. It melts at 219° to 221°C.

EXAMPLE 18

When in Example 2 4,4'-bis-(diethoxyphosphonomethyl)-diphenyl is replaced by an equivalent quantity of 4,4'-bis-(phenylethoxyphosphonomethyl)-diphenyl of the formula (146) 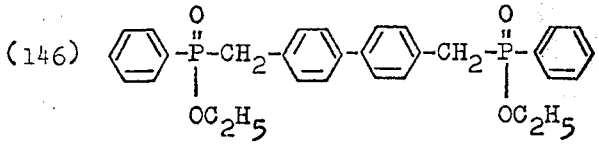

all other reaction and processing conditions being identical, the compound of the formula (78) is obtained in a yield of 23% of the theoretical.

The phosphinic acid ester of the formula (146) used as starting material is obtained by reacting 4,4'-bis-chloromethyl-diphenyl with 2.5 mols of phenyl-diethoxyphosphine. It forms colourless crystals from alcohol, melting at 232° to 234°C.

Analysis: $C_{30}H_{32}O_4P_2$: Calculated: C, 69.49; H, 6.22; P, 11.95%. Found: C, 69.30; H, 6.28; P, 11.93%.

EXAMPLE 19

45.4 Grams of 4,4'-(diethoxyphosphonomethyl)-diphenyl, 13.1 g of p-cyanobenzaldehyde and 21.2 g of the sodium salt of benzaldehyde-2-sulphonic acid (containing 88% of free sulphonic acid) are added to a suspension of 51.1 g of powdered potassium hydroxide (containing about 12% of water) in 200 ml of dimethylformamide, and the mixture is reacted as described in Example 2. After drying, the compound of the formula (120) is removed by boiling with trichlorobenzene, and from the residue, by crystallization from 2 liters of water and 800 ml of dimethylformamide, the compound of the formula (147)

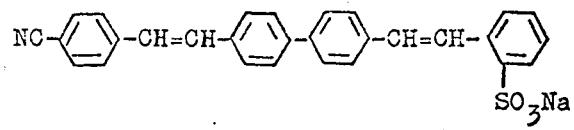

is isolated in form of small, yellow flakes.

Analysis: $C_{29}H_{20}O_3N\ S\ Na.\frac{1}{2}\ H_2O$: Calculated: C, 70.50; H, 4.28; N, 2.83; S, 6.48%. Found: C, 70.41; H, 4.56; N, 2.76; S, 6.65%.

The following asymmetric bis-stilbene compounds of the formulae (148) 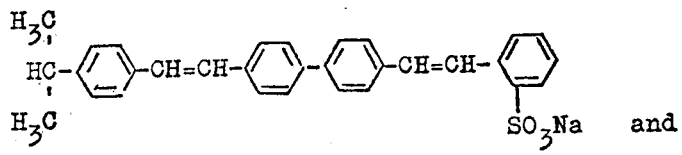

(149) 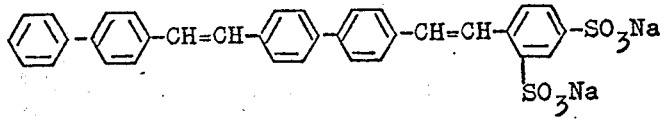

may be prepared in a similar manner.

EXAMPLE 20

A suspension of 22.2 g of the disulphonic acid dichloride of the formula (92) and 0.2 g of a commercial wetting agent in 50 ml of water is stirred into a solution of 40.3 g of sodium sulphite hydrate in ½ liter of water. The reaction mixture is heated to 90°C and at this temperature 15 ml of a 30% aqueous sodium hydroxide solution are dropped in so that the pH value is from 9 to 9.5. After stirring for 12 hours at 90° to 95°C, the hot solution is filtered and the reaction product salted out of the filtrate with 50 g of sodium chloride. After suctioning and drying the resulting disodium salt of the disulphinic acid of the formula (150)

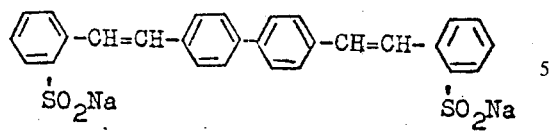

is recrystallized twice from aqueous methanol, and forms light-yellow flakes melting above 300°C.

Analysis: $C_{28}H_{20}O_4S_2Na_2 \cdot 1\ H_2O$: Calculated: C, 61.30; H, 4.04; S, 11.69%. Found: C, 61.47; H, 3.88; S, 12.38%.

16.0 Grams of the disodium salt of disulphinic acid of the formula (150) in 100 ml of water and 150 ml of ethanol are stirred with 50 g of methyliodide for 22 hours at 50°C. The excess methyliodide together with the ethanol is then distilled off and the residual reaction mixture is decolorized with sodium thiosulphate, suctioned and dried under vacuum.

After one recrystallization from ethanol+dimethylformamide +water and two recrystallizations from chloroform+ethanol the compound of the formula (151)

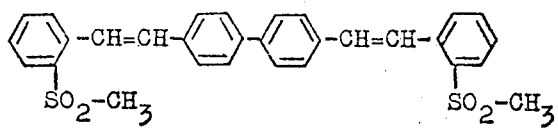

is obtained in form of light-beige, shiny flakes which melt at 301° to 302°C.

Analysis: $C_{30}H_{26}O_4S_2$: Calculated: C, 70.01; H, 5.09; S, 12.46%. Found: C, 69.77; H, 5.03; S, 12.46%.

EXAMPLE 21

A bleached cotton fabric is washed at a goods-to-liquor ratio of 1 : 30 for 30 minutes in a liquid, heated at 60°C, containing per liter:
- 0.032 g of the brightener of the formula 78, 84, 87 or 88
- 1 g of active chlorine (Javelle water)
- 4 g of a washing powder of the following composition
  - 15.00% of dodecylbenzenesulphonate
  - 10.0 % of sodium laurylsulphonate
  - 40.0 % of sodium tripolyphosphate
  - 25.75% of anhydrous sodium sulphate
  - 7.0 % of sodium metasilicate
  - 2.0 % of carboxymethylcellulose and
  - 0.25% of ethylenediamine tetraacetic acid.

After having been rinsed and dried, the fabric displays a strong brightening effect which has good fastness to acids and chlorine.

If desired, the washing powder of the above composition may be incorporated directly with the brightener of the formula (78), (84), (87) or (88).

Strong brightening effects are also obtained when the fabric is washed for 30 minutes at 20°C, or at 95°C without javelle water.

A good brightening effect can be achieved with as little as 0.004 g of whitening agent per liter of washing liquor.

EXAMPLE 22

A bleached cotton fabric is washed at a goods-to-liquor ratio of 1 : 20 for 30 minutes in a liquid, heated at 60° to 95°C, containing per liter:
- 0.04 g of the brightener of the formula (78)
- 4 g of a washing powder of the following composition:
  - 40.0 % of soap flakes
  - 15.0 % of sodium tripolyphosphate
  - 8.0 % of sodium perborate
  - 1.0 % of magnesium silicate
  - 11.0 % of sodium metasilicate (9 $H_2O$)
  - 24.6 % of calcined soda and
  - 0.4 % of ethylenediamine tetraacetic acid.

The rinsed and dried cotton fabric displays a strong brightening effect.

A good brightening effect can be achieved with as little as 0.004 g of whitening agent per liter of washing liquor.

EXAMPLE 23

Cuttings of fabrics of polyamide-6, bleached wool and cotton with "Koratron"-finish are treated at a goods-to-liquor ratio of 1 : 20 for 10 minutes at 30°C in a liquor containing 0.1% of the brightener of the formula (78) referred to the weight of the fibres, and 0.5 g per liter of sodium fluorosilicate.

After having been rinsed and dried, the three types of fibres display a strong brightening effect which has good fastness to light.

EXAMPLE 24

A boiled cotton fabric is treated at a goods-to-liquor ratio of 1 : 30 for 60 minutes at room temperature in a liquor consisting of:
- 0.1% of the brightener of the formula (78) or (87), referred to the weight of the fibre and
- 2 g per liter of active chlorine as Javelle water.

The fabric is then rinsed and dechlorinated. The dried fabric compared with cotton that has not been so brightened, displays a very strong brightening effect.

EXAMPLE 25

A bleached cotton fabric (poplin) is impregnated with a resin+formaldehyde precondensate and ammonium nitrate, the impregnating liquor further containing 1.5 g per liter of the bis-stilbene compound of the formula (78). The fabric is expressed to a weight increase of 80% and the resin is fully condensed for 5 minutes at 150°C. The resulting brilliantly white fabric has good crease-resistance.

Ammonium chloride or sulfate may be used instead of ammonium nitrate.

EXAMPLE 26

A bleached wool fabric is treated at a goods-to-liquor ratio of 1 : 40 for 60 minutes at about 50°C in a bath containing 0.1 to 0.4% of the brightener of the formula (78), (81) or (87), referred to the weight of the fabric, and 4 g of hydrosulphite per liter. After rinsing and drying a strong brightening effect is obtained which has good fastness to light.

A strong brightening effect is also obtained when, instead of hydrosulphite, 5% of acetic acid or formic acid, referred to the weight of the fibre, is added to the liquor.

EXAMPLE 27

A polyamide fiber fabric (Perlon) is immersed at a goods-to-liquor ratio of 1 : 40 at 60°C in a bath which contains (referred to the fabric weight) 0.1% of a brightener of formula (78), (81), (84), (87), (88), (89), (90), (97), (98) or (104) and, per liter, 1 g of 80% acetic acid and 0.25 g of an adduct of 30 – 35 mols of ethylene oxide with 1 mol of commercial stearyl alcohol. The bath is raised to the boil within 30 minutes and maintained at the boil for 30 minutes. The rinsed and dried fabric displays a strong brightening effect of good fastness to light.

When, instead of a fabric of polyamide-6, a fabric of polyamide-66 (nylon) is used, similar, good brightening effects are achieved.

Finally, it is also possible to work under high-temperature conditions, for example for 30 minutes at 130°C; with this variant it is advantageous to add 3 g of hydrosulphite per liter of liquor.

EXAMPLE 28

Polyacrylonitrile fibers (Orlon 42) are immersed at a goods-to-liquor ratio of 1 : 40 in an aqueous bath at 60°C containing per liter 1 g of 85% formic acid and 0.2 % of the compound of the formula (113), (114) or (115a), referred to the fiber weight. The treatment bath is heated within 30 minutes to the boil and maintained at the boil for 30–60 minutes. The rinsed and dried polyacrylonitrile fibers display an outstanding brightening effect.

Good brightening effects are also obtained when Courtelle fibers are treated as described in this Example.

EXAMPLE 29

A polyester fabric (for example Dacron) is padded at room temperature (about 20°C) with an aqueous dispersion containing, per liter, 0.1 to 1 g of the bis-stilbene compound of one of the formulae (101) to (104), (123), (126), (130) or (131), as well as 1 g of an adduct of about 35 mols of ethylene oxide with 1 mol of octadecyl alcohol, and the fabric is dried at about 100°C and then subjected to a heat treatment for 30 seconds at about 220°C, whereupon it displays a strong optical brightening effect.

EXAMPLE 30

A fabric of polyvinylchloride fibres ("Thermovyl") is padded at room temperature (about 20°C) with an aqueous dispersion containing, per liter, 1 to 2 g of the bis-stilbene compound of the formula (138) as well as 1 g of an adduct of about 35 mols of ethylene oxide with 1 mol of octadecyl alcohol and then dried at about 70°C. The dry material is then heat-treated for 3 minutes at 100°C. The polyvinylchloride fibre fabric treated in this manner has a substantially higher white content than an untreated fabric of polyvinylchloride fibres.

EXAMPLE 31

A cellulose acetate fabric is immersed at a goods-to-liquor ratio of 1 : 30 to 1 : 40 at 50°C in an aqueous bath containing 0.15% of the bis-stilbene compound (114), referred to the fibre weight. The treatment bath is then raised to 90° – 95°C and thus maintained for 30 to 45 minutes. After rinsing and drying, a good brightening effect is obtained.

EXAMPLE 32

10 kg of a polyamide (prepared from hexamethylenediamine adipate in known manner) in chip form are mixed with 30 g of titanium dioxide (rutile modification) and 5 g of the compound of formula (78), (107), (109), (119), (99), (120), (123), (128), (130) or (131) for 12 hours in a tumbler. The chips treated in this manner are then melted in a boiler from which the atmospheric oxygen has been displaced by steam and which is heated at 300° – 310°C by oil or diphenyl vapour, and the melt is stirred for half an hour, and then expressed through a spinneret under a nitrogen pressure of 5 atmospheres (gauge). The spun and cooled filament is wound up on a spinning bobbin. The filaments thus obtained display an excellent brightening effect of good fastness to light.

When, instead of a polyamide manufactured from hexamethylenediamine adipate, a polyamide prepared from caprolactam is treated as described, similar, good results are achieved.

EXAMPLE 33

100 Grams of polypropylene (fibre-grade) are intimately mixed with 0.8 g of the compound of the formula (130) or (133) and then melted with stirring at 280° to 290°C. The melt is then spun by a known melt spinning process through conventional spinnerets and stretched. Strongly brightened polypropylene fibers are obtained.

EXAMPLE 34

100 Grams of granulated terephthalic acid ethyleneglycol polyester are intimately mixed with 0.05 g of the compound of the formula (99), (120), (121), (123), (130), (131), (128), (133), (135) or (151) and melted with stirring at 285°C. After spinning from conventional spinnerets strongly brightened polyester fibers are obtained.

If desired, the aforementioned compounds may be added to the starting materials before or during the polycondensation leading to the polyester.

EXAMPLE 35

An intimate mixture of 100 parts of polyvinylchloride, 3 parts of stabilizer (Advastat BD 100; Ba/Cd complex), 2 parts of titanium dioxide, 59 parts of dioctylphthalate and 0.01 to 0.2 part of one of the compounds of the formula (99), (120), (130) or (133) is rolled to and fro on a calender at 150° to 155°C to form a foil. The resulting opaque polyvinylchloride foil has a substantially higher white content than a foil that does not contain the optical brightener.

EXAMPLE 36

100 Parts of polystyrene and 0.1 part of the compound of the formula (99), (119) or (126) is melted with exclusion of air for 20 minutes at 210°C in a tube of 1 cm diameter. After cooling, an optically brightened polystyrene mass of good fastness to light is obtained.

EXAMPLE 37

Paper pulp containing 100 parts of bleached cellulose is mixed in a pulping machine with 2 parts of resin size. After 10–15 minutes a solution of 0.05 to 0.3 part of the compound of the formula (78) in 20 parts of water is added and, 15 minutes later, 3 parts of aluminium sulphate are added. The pulp treated in this manner passes through a mixing vat to a paper-making machine on which paper is made in the usual manner. The resulting paper displays an excellent brightening effect of good fastness to light.

EXAMPLE 38

Paper pulp containing 100 parts of bleached cellulose is mixed in a pulping machine with 2 parts of resin size. After 15 minutes 3 parts of aluminium sulphate are added. The paper web manufactured on a papermaking machine is then superficially sized with a size-press, using as adhesive starch or an alginate containing 0.05 to 0.3 part of the compound of the formula (78) or (81). The resulting paper has a very high white content.

EXAMPLE 39

A solution of 2.6 g of 4-methylbenzaldehyde and 7.75 g of the phosphonium salt of the formula (152)

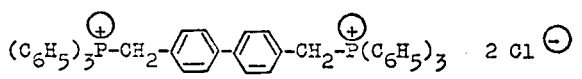

in 100 ml of absolute ethanol is mixed with 2.4 g of potassium tertiary butylate. The yellow solution immediately warms up to about 40°C, and after about one minute a light-beige precipitate forms. The batch is stirred for 3 hours at room temperature, then heated for a short time to 80°C and once more cooled. Suctioning, washing with ethanol and water and drying furnishes 2.7 g of the compound of the formula (119), melting above 300°C.

and 600 ml of de-salted water. After another recrystallization from 600 ml of dimethylformamide and 400 ml of de-salted water, and after drying under reduced pressure at 100° to 110°C, 16.4 g of the compound of the formula (153)

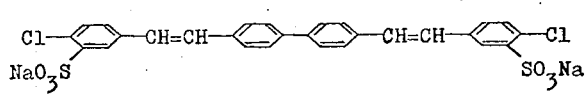

are obtained in the form of a yellow powder.

Instead of 4,4'-bis-(dimethoxyphosphonomethyl)-diphenyl, an equivalent quantity of 4,4'-bis-(diethoxyphosphonomethyl)-diphenyl can be used.

In a similar manner the bis-stilbene compounds of the formula (82)

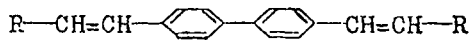

shown in the Table below can be prepared.

| No. | R |
|---|---|
| 154 | 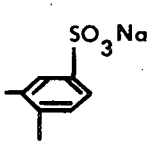 |
| 155 | 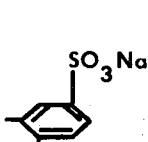 |

The phosphonium salt of the formula (152) is accessible in a yield of 90% by reacting 4,4'-bis-chloromethyl-diphenyl with triphenylphosphine in dimethylformamide. It forms a white powder melting above 300°C.

EXAMPLE 40

While replacing air by a current of nitrogen, a homogeneous mixture of 19.9 g of 4,4'-bis-(dimethoxy-phosphonomethyl)-diphenyl and 24.2 g of the sodium salt of 4-chlorobenzaldehyde-3-sulfonic acid is introduced in the course of 10 minutes into a well-stirred suspension of 6.8 g of sodium methylate (content 95.6%) in 250 ml of anhydrous dimethylformamide. The temperature rises to 45°C and is kept at 40°–45°C by cooling with ice. Stirring is continued at 40°–45°C for 2 hours. The pale-yellow, viscous suspension is poured into 1000 ml of de-salted water, and the suspension is cooled to 15°C while stirring. The product is filtered with suction, washed with 100 ml of de-salted water, and recrystallized from a mixture of 900 ml of dimethylformamide The sulfobenzaldehydes used as starting material for the compound (153), (154) or (155) can be obtained by sulfonation of the corresponding benzaldehydes with oleum having a 66% content of $SO_3$.

EXAMPLE 41

While replacing air by a current of nitrogen, a solution of 136.2 g of 4,4'-bis-(diethoxyphosphonomethyl)-diphenyl and 98.4 g of benzaldehyde-3-carboxylic acid methyl ester in 600 ml of anhydrous dimethylformamide is added dropwise in the course of 10 minutes to a well-stirred suspension of 37.3 g of sodium-methylate (content 95.6%) in 500 ml of anhydrous dimethylformamide. The temperature rises to 45°C and is kept at 40° to 45°C by cooling with ice. Stirring is continued for 1 hour at 40° – 45°C. 500 ml of methanol are added, the crystalline product is filtered off with suction and washed neutral with de-salted water.

Yield: 117.8 g of the compound of the formula (156) 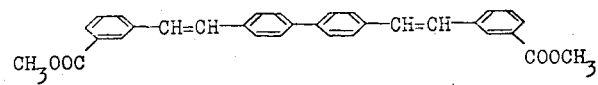

in the form of a pale-yellow powder; melting point, 232°–234°C.

For further purification, the product is recrystallized first from dimethylformamide with the addition of active carbon, then twice from chlorobenzene with the addition of Fuller's earth. The product is obtained in the form of pale-yellow, fine lamellae melting at 236°–237°C.

Instead of dimethylformamide as solvent, there may also be used dimethylsulfoxide, and instead of solid sodium methylate there may be used a methanolic sodiummethylate solution. Likewise, instead of 4,4'-bis-(diethoxyphosphonomethyl)-diphenyl, an equivalent quantity of 4,4'-bis-(dimethoxy-phosphonomethyl)-diphenyl may be used.

In a similar manner, the bis-stilbene compounds of the formula

(82) R—CH=CH—⌬—⌬—CH=CH—R shown in the Table below can be prepared.

| No. | R |
|---|---|
| 157 | —⌬—COOCH$_3$ |
| 158 | ⌬—CH$_3$ |
| 159 | H$_3$C—⌬—CH$_3$ |
| 160 | H$_3$C—⌬—CH$_3$ (2,4) |
| 161 | —⌬—CH$_3$, CH$_3$ |
| 162 | H$_3$C—⌬—CH$_3$, CH$_3$ |
| 163 | H$_3$C—⌬—CH$_3$, CH$_3$ |

EXAMPLE 42

19.0 g of the compound of the formula (156) are stirred in 700 ml of methylcellosolve while being heated to 92°C. To the pale-yellow suspension are added dropwise in the course of 5 minutes 30 g of 30% sodium hydroxide solution. Stirring is continued at 97°–103°C for 1 hour, the pale-yellow suspension is cooled to 20°C, the crystalline product is filtered off with suction, washed with 150 ml of de-salted water, and dried in vacuo at 100°–110°C. Yield: 19.2 g of the compound of the formula (164) 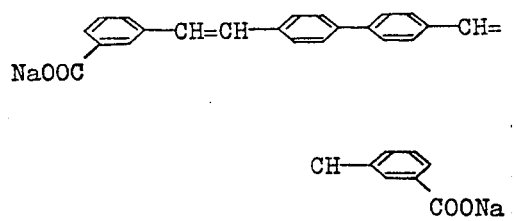

in the form of a pale-yellow powder.

74.2 g of the compound of the formula (164) are suspended with stirring in 500 ml of chlorobenzene and 2 ml of dimethylformamide. In the course of 5 minutes, 100 ml of thionylchloride are added dropwise, the temperature rising from 35° to 45°C. In the course of about 30 minutes, the batch is heated to 110°C, and kept at 105°–110°C for 3 hours. After cooling, the crystalline product is filtered off with suction, recrystallized from 400 ml of chlorobenzene, and dried under reduced pressure at 80°–85°C.

Yield: 45.1 g of the compound of the formula (165) 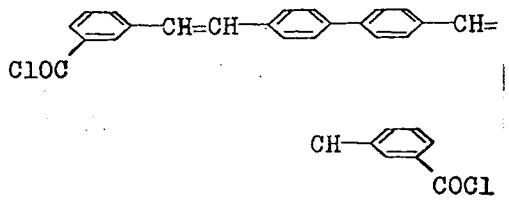

in the form of a pale-yellow powder; melting point: 213° to 214°C.

7.2 g of the compound of the formula (165) are dissolved in 150 ml of chlorobenzene while stirring at 92°C. In the course of 5 minutes, 20 ml of diethanolamine are added dropwise. The batch is stirred fro 4 hours at 90° to 95°C, cooled to 70°C, 100 ml of methanol are added, the mixture is kept at 70°C for 10 minutes, then cooled to 20°C, filtered with suction, and the product recrystallized from a mixture of 100 ml of dimethylsulfoxide and 100 ml of ethanol.

Yield: 7.1 g of the compound of the formula (166) 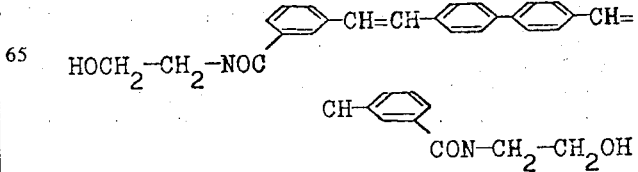

in the form of a pale-yellow powder; melting point: 247°–248°C.

The condensation can also be carried out directly in 100 ml of diethanolamine at about 60°C. For working up, the warm reaction mixture is treated with 50 ml of de-salted water and 200 ml of ethanol, cooled, and the crystalline product filtered off with suction.

EXAMPLE 43

7.25 g of the compound of the formula (165) in 100 ml of pyridine are stirred at 95°–99°C for 1 hour. Then, 100 ml of de-salted water are added dropwise, the pale-yellow suspension is cooled to 20°C and filtered with suction. The product is suspended in de-salted water, neutralized with hydrochloric acid, filtered with suction, washed with de-salted water and dried under reduced pressure. Yield: 6.3 g of the compound of the formula (167)  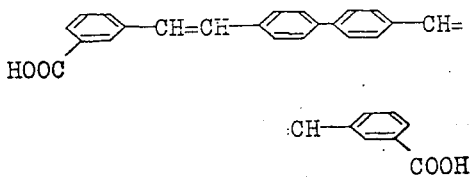

in the form of a pale-yellow powder; melting point: higher than 300°C.

EXAMPLE 44

14.5 g of the compound of the formula (122) are suspended in a mixture of 250 ml of isopropanol and 250 ml of ortho-dichlorobenzene while stirring at 20°C. The whole is heated to 80°C and stirred for 8 hours at 80°–87°C. After cooling, the crystalline product is filtered off with suction and crystallized from 500 ml of ortho-dichlorobenzene with an addition of Fuller's earth. Yield: 5.3 g of the compound of the formula (168)

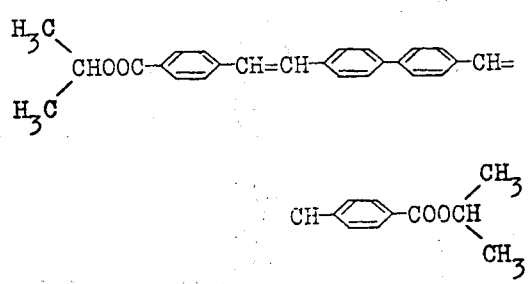

in the form of pale-yellow lamellae; melting point: 290°C (decomposition).

In a manner similar to that described above or in Example 15, the bis-stilbene compounds of the formula

(82)  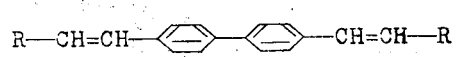

shown in the Table below can be prepared.

| No. | R |
|---|---|
| 169 | —⟨⟩—COOCH$_2$CH$_3$ |
| 170 | —⟨⟩—COOCH$_3$ |
| 171 | —⟨⟩—COOCH$_2$—CH—CH$_2$—CH$_2$—CH$_2$—CH$_3$<br>　　　　　　　　\|<br>　　　　　　　C$_2$H$_5$ |
| 172 | —⟨⟩—CON(CH$_2$—CH$_2$OH)$_2$ |
| 173 | —⟨⟩—CO—N—CH$_2$—CH$_2$OH<br>　　　　\|<br>　　　CH$_3$ |
| 174 | —⟨⟩—CONH—CH$_2$—CH$_2$OH |

| No. | R |
|---|---|
| 175 | -C₆H₄-CON(CH₃)₂ |
| 176 | -C₆H₄-CONH₂ |
| 177 | -C₆H₄-CO-NH-CH₃ |
| 178 | -C₆H₄-CO-N(CH₃)-CH₂-CH₂OH |
| 179 | -C₆H₄-CO-NH-CH₂-CH₂OH |
| 180 | -C₆H₄-CO-N(CH₂CH₂)₂O (morpholinocarbonyl) |
| 181 | -C₆H₄-CO-NH-CH₂-CH(CH₃)-CH₂-CH₂-CH₂-CH₃ |
| 182 | -C₆H₄-CONH-CH₂-CH(C₂H₅)-CH₂-CH₂-CH₂-CH₃ |
| 183 | -C₆H₄-COOC₂H₅ |
| 184 | -C₆H₄-COOCH(CH₃)₂ |
| 185 | -C₆H₄-COOCH₂-CH(C₂H₅)-CH₂-CH₂-CH₂-CH₃ |

EXAMPLE 45

At 45°C, 4.9 g (0.044 mol) of potassium tertiary butylate are stirred into a solution of 6.4 g (0.02 mol) of phosphine oxide of the formula (186)

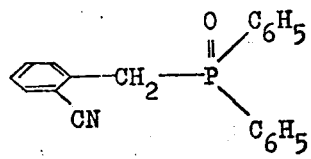

and 2.1 g (0.01 mol) of diphenyl-4,4'-dialdehyde in 100 ml of anhydrous toluene. The mixture is refluxed for 5 hours under nitrogen, then cooled to 5°C and filtered. The residue is washed twice with 10 ml of methanol each time, and repeatedly with water, and dried. There are obtained 2.4 g (59% of the theory) of the dinitrile of the formula (187)

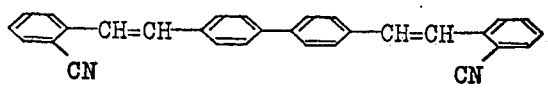

in the form of a pale yellow powder melting at 273°–275°C. Recrystallization from ortho-dichlorobenzene yields 1.5 g of pale yellow lamellae melting at 276°–276.5°C.

The ortho-cyanobenzyl-diphenyl-phosphine oxide of the formula (186) used as starting material can be prepared as follows:

24.3 g (0.11 mol) of para-chloro-diphenylphosphine are added dropwise while stirring (in the course of 15 minutes) under a nitrogen atmosphere, at 110°C, to 19.6 g (0.1 mol) of molten ortho-bromo-methylbenzonitrile in such manner that the temperature does not rise above 120°C. The viscous solution is then heated at 140°C for 15 minutes, when it solidifies completely. After cooling to about 70°C, 50 ml of methanol are added dropwise at such a rate that the evolution of gas can be kept well under control (about 10 minutes). The resulting clear solution is maintained at the reflux temperature for half an hour, 35 ml of water are added, and the batch is then cooled to 0°C. The precipitated product is filtered off with suction, washed with 25 ml of a 1:1 mixture of methanol and water, and dried. There are obtained 24.0 g (76% of the theory) of a crystalline product which melts at 166°–166.5°C. Recrystallization from toluene yields 22.3 g of colorless crystals. Melting point, 167°–167.5°C.

EXAMPLE 46

A suspension of 5.8 g (0.01 mol) of bisphosphine oxide of the formula (188)

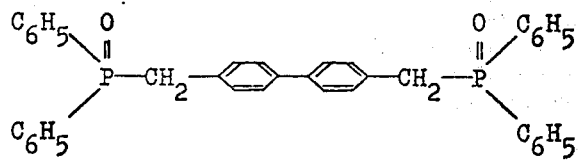

and 4.9 g (0.044 mol) of potassium-tertiary butylate in 100 ml of absolute xylene is stirred while being refluxed under an atmosphere of nitrogen. In the course of 20 minutes, a solution of 3.3 g (0.022 mol) of mesityl aldehyde in 25 ml of absolute xylene is added dropwise, and the mixture is refluxed for 16 hours. The batch is filtered hot, the filtrate is evaporated to dryness under redued pressure, and the residue is recrystallized from 15 ml of methyl cellosolve. There are obtained 1.3 g of crude product of the formula (189)

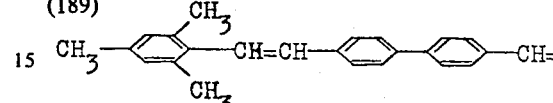

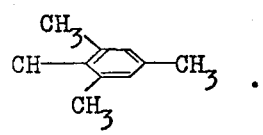

Colorless lamellae from cyclohexane: Melting point, 181°–182°C.

In an analogous manner, using benzaldehyde-2-sulfonic acid (as sodium salt) instead of mesityl aldehyde, and dimethylsulfoxide as solvent, at a temperature of about 70°C, there is obtained the compound of the formula (190)

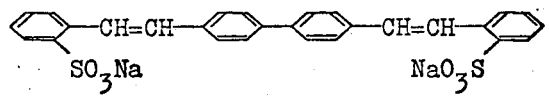

The bisphosphine oxide of the formula (188) used as starting material can be prepared as follows:

A mixture of 25.1 g (0.1 mol) of 4,4'-bis-chloromethyl-diphenyl and 48.5 g (0.22 mol) of para-chloro-diphenylphosphine is slowly heated to 130°C under an atmosphere of nitrogen, while stirring vigorously. Due to the exothermic reaction the temperature rises to 140°C and the mixture solidifies after some time. The mass is kept at 140°C for 2 more hours, then cooled to 40°–50°C, and 100 ml of methanol are added dropwise at such a rate that the evolution of gas is well under control (about 30 minutes). The resulting white crystal magma is refluxed for a few hours until the evaporation of gas ceases. After cooling to room temperature, the batch is filtered and the residue is washed with 2 × 30 ml of methanol and dried. There are obtained 44.7 g (77% of the theory) of a white powder melting at 382°–385°C. On repeated recrystallization from dimethyl sulfoxide, colorless needles are obtained:

| Melting point: | 386 – 387°C | |
|---|---|---|
| Analysis: | $C_{36}H_{32}O_2P_2$ | (582.62) |
| Calculated: | P 10.63% | |
| Found: | P 10.61% | |

EXAMPLE 47

A mixture of 45.5 g of 4,4'-bis-(diethoxy-phosphonomethyl)-diphenyl, 14.1 g of 2-chlorobenzaldehyde and 21.2 g of the sodium salt of benzaldehyde-2-sulphonic acid (with a content corresponding to about 88% of free sulphonic acid) in 150 ml of dimethylformamide is introduced into a well-stirred suspension of 49.2 g of potassium hydroxide powder (about 91% strength) in 200 ml of anhydrous dimethylformamide, with the air being displaced by nitrogen. The temperature rises to 45°C and is kept at 40° to 45°C by ice cooling. The mixture is then stirred for a further 2 hours at 40° to 45°C. The reaction mixture is poured into 2.5 l of distilled water at about 70°c. About 1 kg of ice is added to the resulting cloudy solution, with the temperature of the pale yellow suspension dropping to about 25°C. The pH-value of the suspension is adjusted to about 7 by adding 37% strength hydrochloric acid, the mixture is stirred for a further hour at room temperature and the product is filtered off and washed with 23% strength sodium chloride solution.

The product is dissolved in 750 ml of dimethylformamide at the boil, the cloudy solution is clarified by filtration and the filtrate is cooled. The product which has crystallised out is removed by filtration and the clear filtrate is mixed with 750 ml of distilled water, heated to the boil and clarified by filtration, and the filtrate is cooled. The product which has crystallised out is filtered off and dried in vacuo.

Yield: 10.6 g of the compound of formula (191)

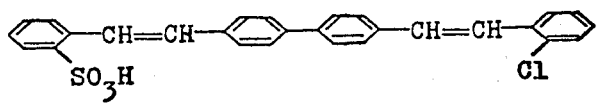

in the form of a sodium/potassium salt mixture, as a pale yellow crystal powder.

In order to manufacture the Compound No. (191) (above) it is also possible, with equally good results, to use the equivalent amount of 4,4'-bis-(dimethoxyphosphonomethyl)-diphenyl instead of the 4,4'-bis-(diethoxyphosphonomethyl)-diphenyl used above. Equally, sodium hydroxide can be employed instead of potassium hydroxide as the alkaline condensation agent. Finally, dimethylsulphoxide can also be used as the solvent instead of dimethylformamide.

The abovementioned 4,4'-bis-(diethoxyphosphonomethyl)-diphenyl of formula (192)

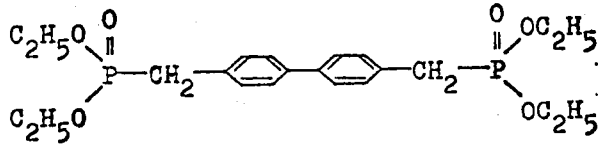

can be obtained by reaction of 4,4'-bis-chloromethyldiphenyl with triethylphosphite at about 140°C, with 2 mols of ethyl chloride being split off.

4,4'-Bis-(dimethoxyphosphonomethyl)-diphenyl of formula (193)

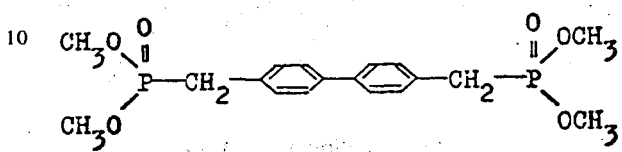

is obtained analogously by reaction of 4,4'-bis-chloromethyl-diphenyl, with trimethylphosphite at about 115°C, with methyl chloride being split off.

EXAMPLE 48

The procedure described in Example 47 is followed, but instead of 2-chlorobenzaldehyde 3-chlorobenzaldehyde is employed. The crude reaction product is worked up as follows:

The filter cake, in a mixture of 500 ml of diemthylformamide and 500 ml of distilled water, is heated to the boil, the cloudy solution is clarified by filtration, the clear filtrate is mixed with 5 g of sodium chloride and cooled, and the product which has crystallised out is filtered off. This is dissolved in 1 l of ethanol at the boil, the solution is clarified by filtration and cooled, and the product isolated by filtration and dried in vacuo at 100° to 110°C.

Yield: 4.8 g of the compound of formula (194)

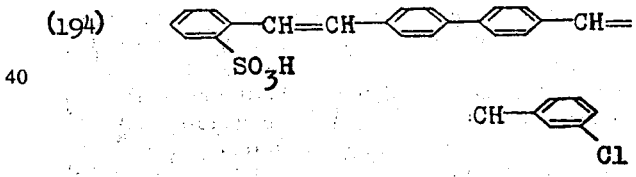

in the form of a sodium/potassium salt mixture, as a pale yellow crystal powder.

The bis-stilbene compounds of formula (195)

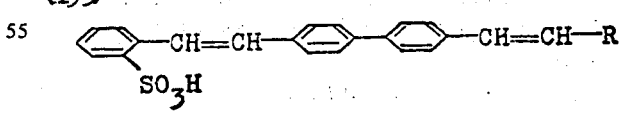

listed in the Table which follows can be manufactured in the form of sodium/potassium salt mixtures in a similar manner to that described in the preceding examples. If the procedure of Example 49 (below) is followed, the corresponding sodium salts are obtained.

| No. | R |
|---|---|
| 196 |  |
| 197 |  |
| 198 | 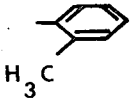 |
| 199 | 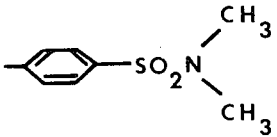 |
| 200 |  |
| 201 | 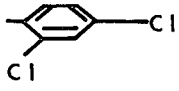 |
| 202 | 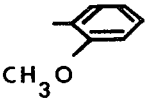 |
| 203 |  |

| No. | R |
|---|---|
| 204 | 2,6-dichlorophenyl (Cl at 2 and 6 positions) |
| 205 | 2,4,6-trimethylphenyl |
| 206 | 2,6-dimethoxyphenyl |
| 207 | naphthyl |
| 208 | 3,4-dichlorophenyl |
| 209 | 3-methylphenyl |

EXAMPLE 49

103 g of a methanolic sodium methylate solution containing 25.2% of sodium methylate, manufactured by dissolving sodium in absolute methanol, are evaporated to dryness in vacuo. The sodium methylate powder thus obtained (commercially available Na methylate can also be used) is suspended in 100 ml of dimethylformamide whilst stirring and displacing the air by a stream of nitrogen. A solution, warmed to about 60°C, of 79.6 g of 4,4'-bis-(dimethoxyphosphonomethyl)-diphenyl, 42.4 of the sodium salt of benzaldehyde-2-sulphonic acid (about 98% content) and 28.7 g of 2-chloro-benzaldehyde in 300 ml of dimethylformamide is added dropwise over the course of about 15 minutes with good stirring. The temperature rises to 45°C and is kept at 40°to 45°C by ice cooling. The mixture is then stirred for a further 2 hours at 40° to 45°C. 400 ml of dimethylformamide and 520 ml of water are added to the reaction mixture which is neutralized with a little concentrated hydrochloric acid and heated to the boil, and the cloudy solution is filtered through a pressure filter and the residue washed with a boiling mixture of 400 ml of dimethylformamide and 260 ml of water. The clear filtrate is cooled and the product which has crystallised out is filtered off and dried in vacuo at 100° to 110°C.

About 41.8 g of the compound of formula (210) 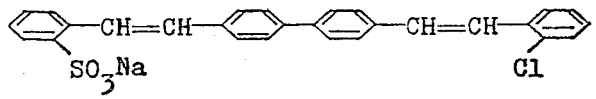

are obtained and can be further purified by recrystallisation from dimethylformamide-water mixture (6:4).

The above procedure can also be modified in that the 4,4'-bis-(dimethoxyphosphonomethyl)-diphenyl, the sodium salt of the benzaldehyde-2-sulphonic acid and the 2-chlorobenzaldehyde are initially introduced into 400 ml of dimethylformamide and the sodium methylate is introduced whilst stirring.

The compound of formula (210) can be converted into the corresponding sulphochloride in a manner which is in itself known, for example by heating to about 100°C in dry chlorobenzene with excess thionyl chloride and a catalytic amount of dimethylformamide. From this sulphochloride, it is for example possible, in a manner which is in itself known, to obtain the dimethylammonium salt by heating in dimethylformamide or the pyridinium salt by heating in pyridine.

The bis-stilbene compound of formula (211) 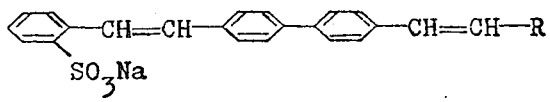

listed in the Table which follows can be manufactured in a corresponding manner.

Table B

| No. | R |
|---|---|
| 212 | —⟨⟩—COOCH$_3$ |
| 213 | —⟨pyridine⟩ |
| 214 | —⟨⟩ with COOCH$_3$ |
| 215 | —⟨⟩—SO$_2$CH$_3$ |
| 216 | —⟨⟩ with F |

| No. | R |
|---|---|
| 217 | 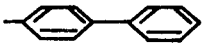 |
| 218 |  |
| 219 | 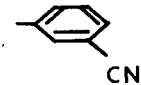 |
| 220 | 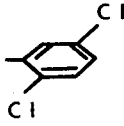 |
| 221 | 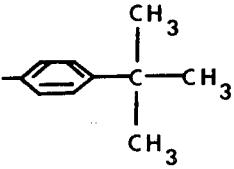 |
| 222 | 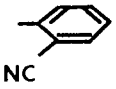 |
| 223 | 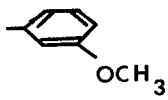 |
| 224 | 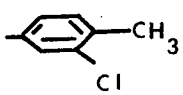 |
| 225 | 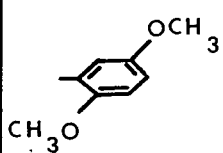 |

| No. | R |
|---|---|
| 226 |  |
| 227 |  |
| 228 |  |
| 229 |  |
| 230 |  |
| 231 |  |
| 232 |  |
| 233 |  |
| 234 | 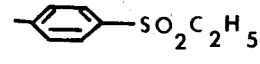 |

| NO. | R |
|---|---|
| 235 | 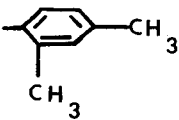 |
| 236 | 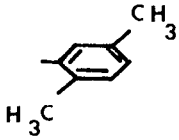 |
| 237 | 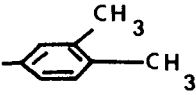 |
| 238 | 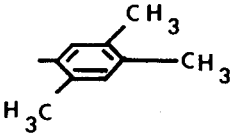 |
| 239 | 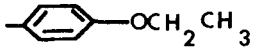 |
| 240 | 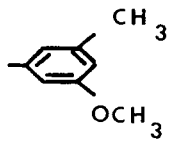 |
| 241 | 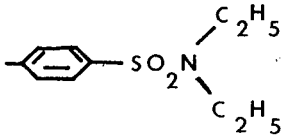 |
The aldehydes used for making compounds 228 and 229 can be made analogously to the starting aldehyde for compound 214.
The bis-stilbene compounds of formula
(242)  $R_1$—CH=CH—⟨⟩—⟨⟩—CH=CH—$R_2$ listed in the Table which follows can be manufactured in a corresponding manner.

ing 66% of $SO_3$. They are isolated and purified via the barium salt.

Table C

| No. | $R_1$ | $R_2$ |
|---|---|---|
| 243 | 4-Cl, 2-($NaO_3S$)-phenyl | phenyl |
| 244 | 4-$CH_3$, 2-($NaO_3S$)-phenyl | 2-Cl-phenyl |
| 245 | 4-$CH_3$, 2-($NaO_3S$)-phenyl | phenyl |
| 246 | 4-Cl, 2-($NaO_3S$)-phenyl | 2-Cl-phenyl |
| 247 | 3-Cl, 4-($NaO_3S$)-phenyl | phenyl |
| 248 | 3-Cl, 4-($NaO_3S$)-phenyl | 3-$OCH_3$-phenyl |

The sulphobenzaldehydes employed can be obtained in a manner which is in itself known by sulphonation of the corresponding benzaldehydes with oleum contain-

EXAMPLE 50

55.5 g of the disulphochloride of formula

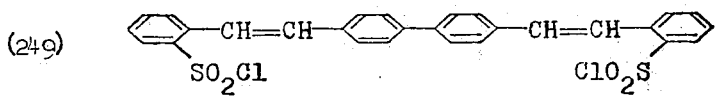

(249)

are dissolved in 1500 ml of anhydous o-dichlorobenzene at 80°C. 15.6 g of a 28.9% strength anhydrous solution of dimethylamine in ethanol are added dropwise over the course of 15 minutes. The mixture is stirred for a further hour at 75° to 80°C and filtered through a pressure filter, the filtrate is cooled and the product which has crystallised out is filtered off. The product which has been filtered off is boiled for 1 hours in 500 ml of pyridine at the reflux temperature, the cloudy solution is clarified by filtration, the filtrate is cooled and the product which has crystallised out is filtered off. This product is boiled in 200 ml of water, the mixture is rendered alkaline with sodium hydroxide solution and clarified by filtration through a pressure filter, the filtrate is cooled to 50°C and the product which has crystallised out is filtered off and dried in vacuo at 100° to 110°C.

The compound of formula

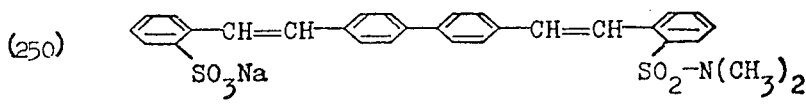

is obtained in a yellow powder.

The disulphochloride of formula (240) was obtained from the compound of formula

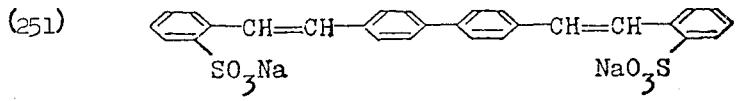

by reaction with thionyl chloride with the addition of a catalytic amount of dimethylformamide in anhydrous chlorobenzene at 95° to 100°C. the Compound (251) can for example be obtained by condensation of 1 mol of 4,4'-bis-(diethoxyphosphonomethyl)-diphenyl with 2 mols of the sodium salt of 2-sulphobenzaldehyde in dimethylformamide in the presence of about 8 mols of potassium hydroxide powder (about 90% strength).

EXAMPLE 51

Bleached cotton fabric is washed for 15 minutes, using a liquor ratio of 1:20, in a liquor warmed to 50°C which per liter contains the following additives: 0.004 to 0.016 g of the brightener of formula (191), (194), (196), (197), (198), (200), (202), (203), (206), (208), (209) and (223), 0.25 g of active chlorine (Javelle water), and 4 g of a washing powder of the following composition: 15.00% of dodecylbenzenesulphonate, 10.00% of sodium laurylsulphonate, 40.00% of sodium tripolyphosphate, 25.75 % of anhydrous sodium sulphate, 7.00 % of sodium metasilicate, 2.00 % of carboxymethylcellulose and 0.25 % of ethylenediaminetetraacetic acid. In doing so, the cotton fabric is only introduced into the bath 15 minutes after preparation of the washing bath warmed to 50°C. After rinsing and drying, the fabric shows a good brightening effect of good fastness to acid, light and chlorine.

A good brightening effect is also achieved if the washing process is carried out in the same manner for 15 minutes at 25°C.

The washing powder of the abovementioned composition can also contain the brighteners of the above formulae directly incorporated.

EXAMPLE 52

A polyamide fibre fabric (Perlon-Helanca) is washed for 15 minutes, using a liquor ratio of 1:20, in a liquor warmed to 50°C which per liter contains the following additives: 0.004 to 0.016 g of the brightener of formulae (191), (194), (196), (197), (198), (199), (200), (201), (202), (203), (206), (208), (209) and (223), 0.25 g of active chlorine (Javelle water), and 4 g of a washing powder of the following composition: 15.00 % of dodecylbenzenesulphonate, 10.00 % of sodium laurylsulphonate, 40.00 % of sodium tripolyphosphate, 25.75 % of anhydrous sodium sulphate, 7.00 % of sodium metasilicate, 2.00 % of carboxymethylcellulose and 0.25 % of ethylenediaminetetraacetic acid. The polyamide fibre fabric is only introduced into the washing bath, warmed to 50°C, 15 minutes after preparation of the latter. After rinsing and drying the fabric shows a good brightening effect of good fastness to light.

A good brightening effect is also achieved if the washing process is carried out in the same manner but at 25°C.

The washing powder of the abovementioned composition can also contain the brighteners of the above formulae directly incorporated.

EXAMPLE 53

A polyamide fiber fabric (Perlon) is introduced at 60°C, using a liquor ratio of 1:40, into a bath which (relative to the weight of fabric) contains 0.1% of one of the brighteners of formulae (191), (194), (196), (197), (198), (199), (200), (201), (202), (203), (206), (208), (209) and (223) and also contains 1 g of 80% strength acetic acid and 0.25 g of an addition product of 30 to 35 mols of ethylene oxide to one mol of technical stearyl alcohol per liter. The bath is heated to the boil over the course of 30 minutes and is kept at the boil for 30 minutes. After rinsing and drying a good brightening effect is achieved.

If instead of the fabric of polyamide-6 a fabric of polyamide-66 (nylon) is used, similar brightening effects are obtained.

Finally, it is also possible to work under high temperature conditions, for example for 30 minutes at 130°C. For this type of use, it is advisable to add 3 g/l of hydrosulfite to the liquor.

EXAMPLE 54

10,000 g of a polyamide manufactured from hexamethylene-diamine adipate in a known manner, in chip form, are mixed for 12 hours in a tumbler vessel with 30 g of titanium dioxide (rutile modification) and 5 g of one of the compounds of formulae (191), (194), (196), (197), (198), (200), (201), (202), (206), (208), (209) and (223). The chips treated in this way are fused in a kettle heated to 300° – 310°C with oil or diphenyl vapour, after displacing the atmospheric oxygen by steam, and are stirred for half an hour. The melt is thereafter extruded through a spinneret under a nitrogen pressure of 5 atmospheres gauge and the filament which has been spun in this way and cooled is wound up on a spinning bobbin. The resulting filaments show a good brightening effect.

If instead of a polyamide manufactured from hexamethylenediamine adipate a polyamide manufactured from ε-caprolactam is used, similarly good results are obtained.

EXAMPLE 55

A cotton fabric article provided with a non-iron finish by means of an aminoplastic resin is washed for 15 minutes, using a liquor ratio of 1:20, in a liquor warmed to 40°C which per liter contains the following additives: 0.004 to 0.016 g of a brightener of formulae (191), (194), (196), (198) and (223), and 4 g of a washing powder of the following composition: 15.00 % of dodecylbenzenesulphonate, 10.00 % of sodium laurylsulphonate, 40.00 % of sodium tripolyphosphate, 25.75 % of anhydrous sodium sulphate, 7.00 % of sodium metasilicate, 2.00 % of carboxymethylcellulose and 0.25 % of ethylenediaminetetraacetic acid. After rinsing and drying the fabric shows a higher white content in daylight than does the untreated material.

EXAMPLE 56

46.0 g of the compound of the formula (252) 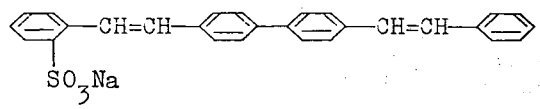

in 500 ml of chlorobenzene and 100 ml of thionyl chloride, with the addition of 1 ml of dimethylformamide are converted into the sulfochloride of the formula (253) 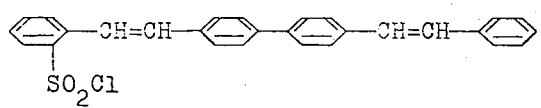

in the manner described in Example 4.

Yield: 28.9 g; melting point: 229°C (decomposition).

20.0 g of the compound of the formula (253) are introduced while stirring into 200 ml of 3-dimethylamino-1-propylamine. The mixture is then heated to 55°C and stirred for 1 hour at 55°– 60°C. 200 ml of water and 100 ml of ethanol are added, stirring is continued for 30 minutes at 55° to 60°C, followed by cooling to 20°C. The batch is then filtered with suction, washed with water, then with ethanol, and the product recrystallized from a mixture of 250 ml of ethanol and 200 ml of dioxan.

Yield: 20.2 g of the compound of the formula (254) 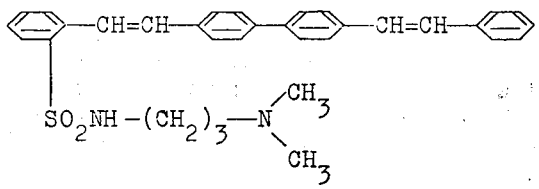

in the form of a pale-yellow powder; melting point: 165° to 166°C.

EXAMPLE 57

13 g of the compound of the formula (254) in 1000 ml of methanol are refluxed with 10 ml of dimethylsulfate while stirring for 3 hours. The mixture is then cooled to 20°C, the product filtered off with suction, washed with methanol, and dried at 80°–85°C under reduced pressure.

Yield: 14.4 g of the compound of the formula (255) 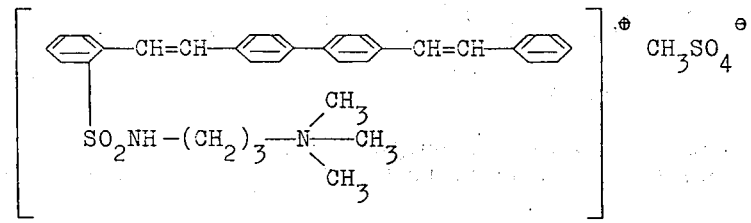

in the form of a pale-yellow powder; melting point: 238°–240°C.

EXAMPLE 58

At 20°C a bleached cotton fabric is introduced at a liquor ratio of 1:30 into a bath which contains (calculated on the weight of the fabric) 0.05 – 0.2% of the fluorescent whitening agent of the formula (78), (84), (87), (88), (89), (153), (154) or (155) and 5 g per liter of crystalline sodium sulfate. The batch is heated to 50°C in the course of 15 minutes, then kept at that temperature for 15 minutes. A strong brightening effect is obtained.

We claim:
1. A bis-stilbene compound of the formula

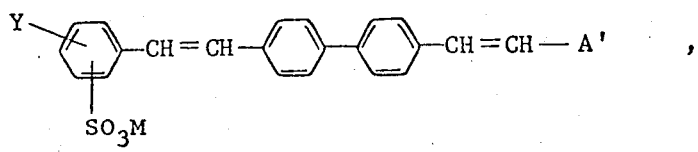

wherein A' represents an α-naphthyl, β-naphthyl, pyridyl or 4-diphenylyl radical or a radical of formula

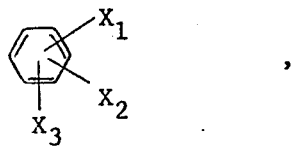

wherein $X_1$ represents hydrogen, an alkyl group containing 1 to 4 carbon atoms halogen or alkoxy with 1 to 4 carbon atoms, $X_2$ and $X_3$ represent hydrogen, an alkyl group containing 1 to 4 carbon atoms, halogen, or alkoxy with 1 to 4 carbon atoms or $X_2$ together with $X_3$ forms a methylenedioxy group, M represents a salt-forming cation and Y represents a hydrogen atom, halogen, an alkyl group containing 1 to 4 carbon atoms or an alkoxy group containing 1 to 4 carbon atoms.

2. A bis-stilbene compound according to claim 1, which corresponds to the formula

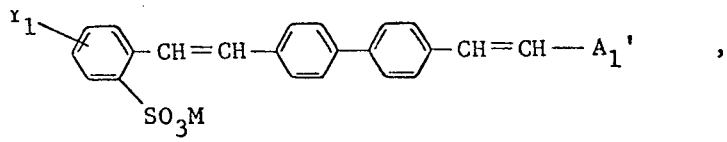

wherein $A_1'$ represents a β-naphthyl, pyridyl or 4-diphenylyl radical or a radical of formula

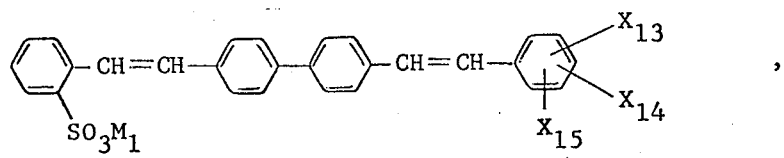

wherein $X_7$ represents hydrogen, an alkyl group containing 1 to 4 carbon atoms fluorine or chlorine or alkoxy with 1 to 4 carbon atoms, $X_8$ and $X_9$ represent hydrogen, an alkyl group containing 1 to 4 carbon atoms, fluorine or chlorine and $X_8$ is also alkoxy with 1 to 4 carbon atoms, M represents a salt-forming cation and $Y_1$ represents a hydrogen atom, fluorine or chlorine, an alkyl group containing 1 to 4 carbon atoms or an alkoxy group containing 1 to 4 carbon atoms.

3. A bis-stilbene compound according to claim 2, wherein $X_7$ denotes hydrogen, methyl, tert. butyl, fluorine, chlorine or alkoxy with 1 to 4 carbon atoms, $X_8$ denotes hydrogen, methyl, tert, butyl, fluorine, chlorine or alkoxy with 1 to 4 carbon atoms and $X_9$ denotes hydrogen, methyl, fluorine or chlorine, M represents a salt-forming cation from the group consisting of hydrogen ion, alkali metal ion, ammonium ion or amine salt ion and $Y_1$ represents a hydrogen atom, fluorine, chlorine, an alkyl group containing 1 to 4 carbon atoms or an alkoxy group containing 1 to 4 carbon atoms.

4. A bis-stilbene compound according to claim 1, which corresponds to the formula

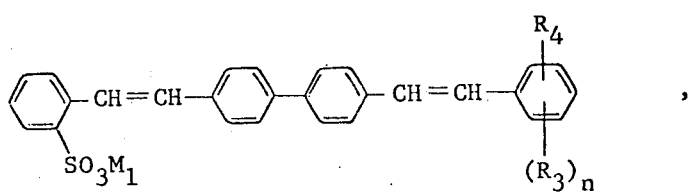

wherein $X_{13}$ denotes hydrogen, methyl, alkoxy with 1 to 4 carbon atoms, or chlorine, $X_{14}$ denotes hydrogen, methyl, alkoxy with 1 to 4 carbon atoms or chlorine, $X_{15}$ denotes hydrogen or methyl and $M_1$ represents a salt-forming cation from the group of hydrogen ion, alkali metal ion, ammonium ion or amine salt ion.

5. A bis-stilbene compound according to claim 1, which corresponds to the formula

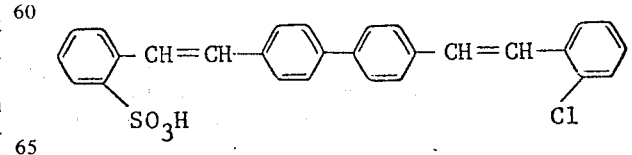

wherein $R_3$ represents hydrogen or methyl, methoxy or chlorine, n denotes the numbers 1 or 2, with $R_3$ being in the m-position, $R_4$ denotes hydrogen, fluorine, and $M_1$ represents a salt-forming cation from the group of hydrogen ion, alkali metal ion, ammonium ion or amine salt ion.

6. A compound as claimed in claim 1, having the formula

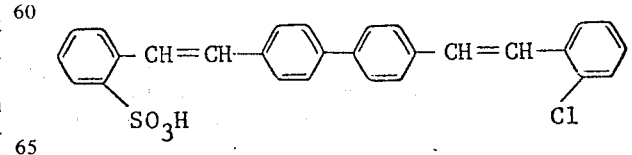

or an alkali metal salt thereof.

7. A compound as claimed in claim 1, having the formula

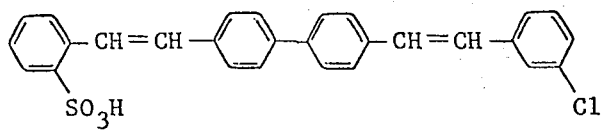

or an alkali metal salt thereof.

8. A compound as claimed in claim 1, having the formula

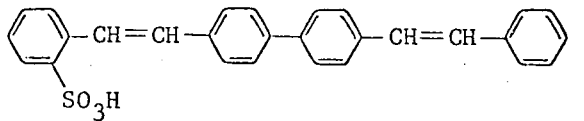

or an alkali metal salt thereof.

9. A compound as claimed in claim 1, having the formula

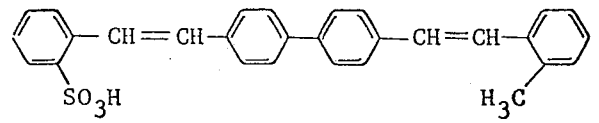

or an alkali metal salt thereof.

10. A compound as claimed in claim 1, having the formula

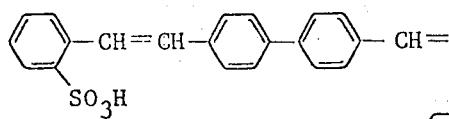

or an alkali metal salt thereof.

11. A symmetrical bis-stilbene compound of the formula

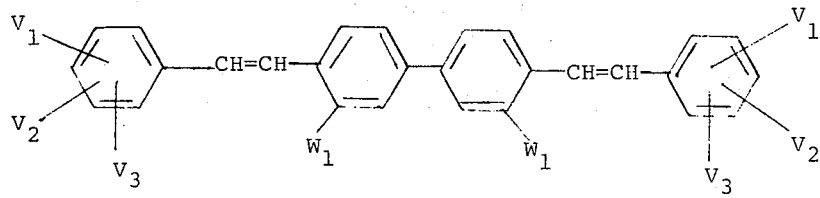

in which
 $V_1$ represents hydrogen or a substituent Q representing a member selected from the group consisting of a sulphonic acid group or a salt thereof;
 $V_2$ represents hydrogen, an alkyl group with 1 to 18 carbon atoms, an alkoxy group with 1 to 12 carbon atoms, halogen or a sulphonic acid group or a salt thereof;
 $V_3$ represents hydrogen or an alkyl group with 1 to 4 carbon atoms;
 $W_1$ represents an alkyl group containing 1 to 4 carbon atoms, an alkoxy group with 1 to 4 carbon atoms, halogen, or a substituent Q representing a member selected from the group consisting of a sulphonic acid group or a salt thereof, on condition that at least one of the symbols $V_1$ or $W_1$ has the significance of a substituent Q.

12. A symmetrical bis-stilbene compound according to claim 11, of the formula

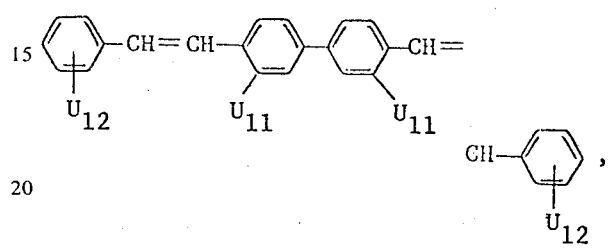

in which one of the symbols $U_{11}$ or $U_{12}$ is a sulphonic acid group or its salts and the other represents a chlorine atom or an alkyl group with 1 to 4 carbon atoms.

13. A symmetrical bis-stilbene compound according to claim 11, of the formula

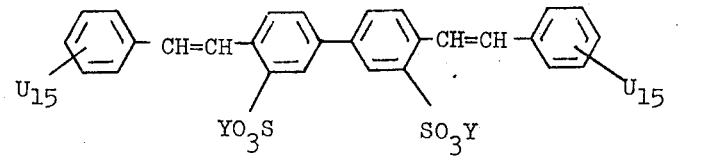

in which $U_{15}$ represents a hydrogen or chlorine atom, an alkyl or alkoxy group with up to 4 carbon atoms, and Y is a cation, selected from the group consisting of hydrogen, alkali metal, ammonia, amine, barium and calcium.

14. A symmetrical bis-stilbene compound of the formula

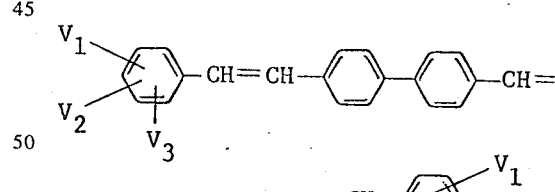

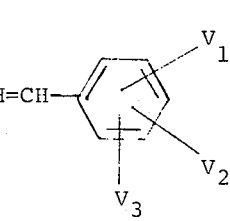

in which $V_1$ represents a sulphonic acid group or a salt, or an ester, thereof; $V_2$ represents hydrogen, an alkyl group with 1 to 18 carbon atoms, an alkoxy group with 1 to 12 carbon atoms, halogen or a sulphonic acid group or a salt, ester thereof, and $V_3$ stands for hydrogen or an alkyl group with 1 to 4 carbon atoms.

15. A symmetrical bis-stilbene compound according to claim 14, wherein $V_1$ represents a sulphonic acid group or a salt thereof, $V_2$ represents hydrogen, an alkyl group with 1 to 18 carbon atoms, an alkoxy group with 1 to 12 carbon atoms, halogen or a sulphonic acid group or a salt or ester thereof, and $V_3$ stands for hydrogen or an alkyl group with 1 to 4 carbon atoms.

16. A symmetrical bis-stilbene compound according to claim 14, of the formula

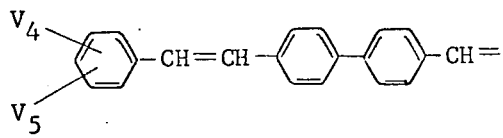

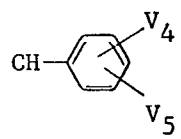

in which $V_4$ represents a sulphonic acid group or a salt or ester thereof; and $V_5$ represents hydrogen, a sulphonic acid group or a salt or ester thereof; an alkyl group with 1 to 4 carbon atoms or an alkoxy group with 1 to 4 carbon atoms.

17. A symmetrical bis-stilbene compound according to claim 14, of the formula

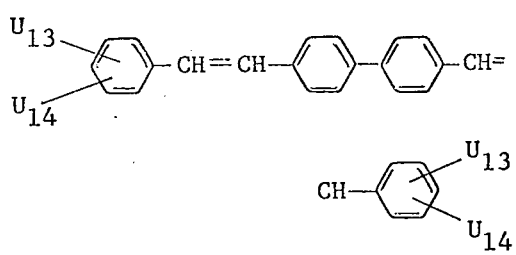

in which $U_{13}$ represents a sulphonic acid group or its salt and $U_{14}$ a hydrogen or chlorine atom or an alkyl group with 1 to 4 carbon atoms.

18. A symmetrical bis-stilbene compound according to claim 14, of the formula

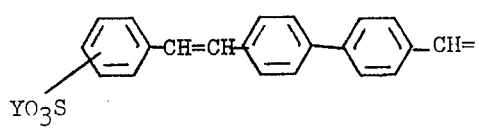

in which Y represents a cation selected from the group consisting of hydrogen, alkali metal, ammonium, amine, barium and calcium and the $YO_3S-$ groups are preferably in the ortho-position relatively to the —CH— groups.

19. A symmetrical bis-stilbene compound according to claim 14, of the formula

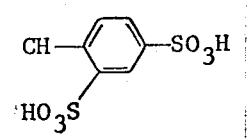

in which $V_6$ represents a sulphonic acid group or a salt thereof.

20. A compound as claimed in claim 14, having the formula

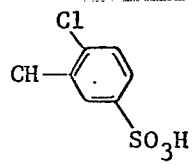

or an alkali metal salt thereof.

21. A compound as claimed in claim 14, having the formula

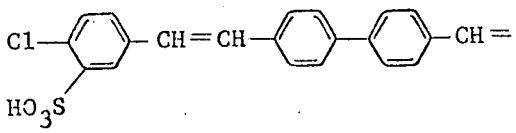

or an alkali metal salt thereof.

22. A compound as claimed in claim 14, having the formula or an alkali metal salt thereof.

23. A compound as claimed in claim 14, having the formula or an alkali metal salt thereof.

* * * * *